(12) United States Patent
Kim et al.

(10) Patent No.: US 11,612,620 B2
(45) Date of Patent: Mar. 28, 2023

(54) PHARMACEUTICAL COMPOSITION FOR PREVENTING OR TREATING RHEUMATOID ARTHRITIS COMPRISING NASAL INFERIOR TURBINATE-DERIVED MESENCHYMAL STEM CELLS AS AN ACTIVE INGREDIENT

(71) Applicant: CATHOLIC UNIVERSITY INDUSTRY ACADEMIC COOPERATION FOUNDATION, Seoul (KR)

(72) Inventors: Sung Won Kim, Seoul (KR); Seung Ki Kwok, Seoul (KR); Jaeseon Lee, Seoul (KR); Sun hwa Park, Seoul (KR); Jung Yeon Lim, Seoul (KR)

(73) Assignee: CATHOLIC UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 133 days.

(21) Appl. No.: 16/633,618

(22) PCT Filed: Jun. 21, 2018

(86) PCT No.: PCT/KR2018/007024
§ 371 (c)(1),
(2) Date: Jan. 24, 2020

(87) PCT Pub. No.: WO2019/022386
PCT Pub. Date: Jan. 31, 2019

(65) Prior Publication Data
US 2020/0254024 A1 Aug. 13, 2020

(30) Foreign Application Priority Data

Jul. 28, 2017 (KR) ........................ 10-2017-0096321
Jun. 18, 2018 (KR) ........................ 10-2018-0069905

(51) Int. Cl.
*A61K 35/28* (2015.01)
*A61P 19/02* (2006.01)

(52) U.S. Cl.
CPC .............. *A61K 35/28* (2013.01); *A61P 19/02* (2018.01)

(58) Field of Classification Search
CPC ................................ A61K 35/28; A61P 19/02
See application file for complete search history.

(56) References Cited

FOREIGN PATENT DOCUMENTS

| CN | 106282108 A | 1/2017 |
|----|-------------|--------|
| CN | 106282108 A | 1/2017 |
| KR | 101327076 B1 | 9/2011 |
| KR | 20110106235 | * 9/2011 |
| KR | 101327076 B1 | 11/2013 |
| KR | 101636139 B1 | 3/2015 |
| KR | 101636139 B1 | 7/2016 |

OTHER PUBLICATIONS

Hwang et al., PLoS One, 2014, vol. 9(6), e100219, p. 1-7.*
Kumar et al., Biomed. Pharmacother., 2016, vol. 79:52-61.*
Kwon et al., Biomaterials, 2014, vol. 35(20):5337-5346.*
R.O. Williams, Methods Mol. Med., 2004, vol. 98:207-216 (abstract).*
Park et al., Cell Transplant., 2016, vol. 25(6):1057-1072, Epub. Apr. 7, 2015.*
Hwang et al., Otolaryngology—Head and Neck Surgery, 2012, vol. 147(3):568-574.*
Singh et al., Biol. Reprod., 1997, vol. 56(6):1370-1375. (abstract).*
Oida et al., J. Immunol. Methods, 2010, vol. 362(1-2):195-198.*
Hwang, Se Hwan et al., "Characteristics of mesenchymal stem cells originating from the bilateral inferior turbinate in humans with nasal septal deviation", PLoS One, 2014, vol. 9(6), e100219, pp. 1-7.
Park, Kyu-Hyung et al., "Treatment of Collagen-Induced Arthritis Using Immune Modulatory Properties of Human Mesenchymal Stem Cells", Cell Transplantation, 2016, vol. 25, pp. 1063-1064.
Zhang, Li et al., "Use of immune modulation by human adipose-derived mesenchymal stem cells to treat experimental arthritis in mice", Americal Journal of Translational Research, May 2017, vol. 9(5), pp. 2595-2607.

* cited by examiner

*Primary Examiner* — Xiaozhen Xie
(74) *Attorney, Agent, or Firm* — Riverside Law LLP

(57) ABSTRACT

The present invention relates to a pharmaceutical composition for preventing or treating rheumatoid arthritis, and a stem cell therapeutic agent for treating rheumatoid arthritis, comprising nasal inferior turbinate-derived mesenchymal stem cells as an active ingredient. Nasal inferior turbinate-derived mesenchymal stem cells of the present invention have the effects of reducing the production of interleukin-17A (IL-17A), tumor necrosis factor-α (TNF-α), immunoglobulin G2 (IgG2a) which is an inflammation-inducing factor, and/or the proliferative ability of lymph node T cells, increasing interleukin-10 (IL-10) and/or regulatory T-cells (Treg, $CD4^+CD25^+foxp3^+$ cell) that contribute to immune tolerance in spleen cells, and inhibiting the proliferation of human T-cells. The nasal inferior turbinate-derived mesenchymal stem cells have a safer acquisition process than existing mesenchymal stem cells and can be acquired in sufficient amounts within a desired period of time, thus allowing mesenchymal stem cells to be acquired at low cost and high efficiency. Moreover, since the nasal inferior turbinate-derived mesenchymal stem cells have the same genetic origin as individuals administered therewith there are few side effects, the nasal inferior turbinate-derived mesenchymal stem cells can be usefully used for preventing or treating in individually tailored immunocompatible rheumatoid arthritis.

8 Claims, 23 Drawing Sheets
Specification includes a Sequence Listing.

PHARMACEUTICAL COMPOSITION FOR PREVENTING OR TREATING RHEUMATOID ARTHRITIS COMPRISING NASAL INFERIOR TURBINATE-DERIVED MESENCHYMAL STEM CELLS AS AN ACTIVE INGREDIENT

CROSS-REFERENCE TO RELATED APPLICATIONS

This application is the U.S. national phase application filed under 35 U.S.C. § 371 claiming benefit to International Patent Application No. PCT/KR2018/007024, filed on Jun. 21, 2018, which claims priority to Korean Patent Application No. 10-2017-0096321, filed Jul. 28, 2017, and Korean Patent Application No. 10-2018-0069905, filed Jun. 18, 2018, the disclosures of which are incorporated herein by reference in their entirety.

TECHNICAL FIELD

The present invention relates to a pharmaceutical composition for preventing or treating rheumatoid arthritis, which includes a nasal inferior turbinate-derived mesenchymal stem cells as an active ingredient, and the like.

BACKGROUND ART

Mesenchymal stromal cells can be obtained from adult bone marrow, inhaled adipose tissue, umbilical cord blood, the umbilical cord, and the like and have the form of fibroblasts. These cells are able to proliferate indefinitely in vitro, and unlike blood stem cells, the cells may differentiate into various types of important cell lines such as fat, osteocytes, chondrocytes, cardiomyocytes, neurons, and the like, and thus research has been actively conducted in the fields of tissue engineering and regenerative medicine.

Nasal inferior turbinate tissue is a small, shell-like independent bone on the lower lateral side of both right and left sides of the nasal cavity and is attached to the maxilla and palatine bones. The inventors of the present invention have recently reported that mesenchymal stem cells isolated from nasal inferior turbinate tissues are able to differentiate into chondrocytes, osteocytes, adipocytes, and neurons (KR 10-1327076).

Meanwhile, rheumatoid arthritis is an autoimmune disease and a chronic inflammatory disease associated with chronic inflammation of joints. Inflammation often spreads to tissues around the joints and other organs. Generally, rheumatoid arthritis is a progressive disease that can lead to joint destruction and dysfunction, and joint inflammation associated with rheumatoid arthritis causes swelling, pain, stiffness and redness of the joint. Joint inflammation associated with rheumatoid arthritis may also occur in tissues around the joint (tendons, ligaments, and muscles). In some patients with rheumatoid arthritis, chronic inflammation destroys cartilage, bones, and ligaments, causing joint deformities. Damage to joints may occur in an early stage of the disease and may be progressive. Progressive damage to the joints does not necessarily correlate with the degree of pain, stiffness, or edema occurring in the joints.

Various clinical treatments for rheumatoid arthritis have been developed, which are divided into general conservative therapy, pharmacotherapy, and surgical therapy. In general, since rheumatoid arthritis causes joint pain, joint deformities, and the loss of joint function, which occur due to chronic arthritis, the treatment of rheumatoid arthritis aims for a return to normal life by suppressing pain and inflammation and minimizing the loss of joint function.

Among currently used treatment methods for rheumatoid arthritis, pharmacotherapy is unable to efficiently inhibit joint destruction even when a combination of three or more of drugs are used for treatment, thus being non-efficient, may cause side effects such as infection, gastrointestinal bleeding or perforation, deterioration of kidney and liver functions, osteoporosis, or Cushing's syndrome, and has a problem of high cost.

Therefore, there is an urgent need to develop a novel material for the prevention or treatment of rheumatoid arthritis, which addresses these problems.

DISCLOSURE

Technical Problem

As a result of having conducted studies to develop a novel therapeutic agent which is effective against rheumatoid arthritis, the inventors of the present invention experimentally verified that a nasal inferior turbinate-derived mesenchymal stem cell is effective in the treatment of rheumatoid arthritis, and thus completed the present invention.

Therefore, an object of the present invention is to provide a pharmaceutical composition for preventing or treating rheumatoid arthritis, which includes nasal inferior turbinate-derived mesenchymal stem cells as an active ingredient.

Another object of the present invention is to provide a stem cell therapeutic agent for treating rheumatoid arthritis, which includes nasal inferior turbinate-derived mesenchymal stem cells as an active ingredient.

However, technical problems to be solved by the present invention are not limited to the above-described technical problems, and other unmentioned technical problems will become apparent from the following description to those of ordinary skill in the art.

Technical Solution

To achieve the above-described objects of the present invention, the present invention provides a pharmaceutical composition for preventing or treating rheumatoid arthritis, which includes nasal inferior turbinate-derived mesenchymal stem cells as an active ingredient.

In one embodiment of the present invention, the rheumatoid arthritis may be collagen-induced arthritis.

In another embodiment of the present invention, the mesenchymal stem cells may reduce the production of interleukin-17A (IL-17A), tumor necrosis factor-$\alpha$ (TNF-$\alpha$), immunoglobulin G2 (IgG2a) which is an inflammation-inducing factor, and/or the proliferative ability of lymph node T cells, and may increase interleukin-10 (IL-10) and/or regulatory T cells (Treg, $CD4^+CD25^+foxp3^+$ cell) contributing to immune tolerance among spleen cells.

In another embodiment of the present invention, the nasal inferior turbinate-derived mesenchymal stem cells may inhibit the proliferation of $CD4^+T$ cells.

The present invention also provides a stem cell therapeutic agent for treating rheumatoid arthritis, which includes nasal inferior turbinate-derived mesenchymal stem cells as an active ingredient.

The present invention also provides a method of preventing or treating rheumatoid arthritis, including administering the pharmaceutical composition for preventing or treating rheumatoid arthritis to a subject.

The present invention also provides a use of a composition including nasal inferior turbinate-derived mesenchymal stem cells as an active ingredient for preventing or treating rheumatoid arthritis.

Advantageous Effects

Nasal inferior turbinate-derived mesenchymal stem cells according to the present invention has the effects of reducing the production of interleukin-17A (IL-17A), tumor necrosis factor-α (TNF-α), immunoglobulin G2 (IgG2a) which is an inflammation-inducing factor, and the proliferative ability of lymph node T cells, and increasing interleukin-10 (IL-10) and regulatory T cells (Treg, $CD4^+CD25^+foxp3^+$ cell) contributing to immune tolerance among spleen cells, and while existing mesenchymal stem cells are accompanied by severe pain in an acquisition process and are time-consuming and cost-consuming in a process of culturing a sufficient amount thereof, the nasal inferior turbinate-derived mesenchymal stem cells according to the present invention can be safely acquired and obtained in a sufficient amount at a desired time, and thus the nasal inferior turbinate-derived mesenchymal stem cells can be obtained at low cost with high efficiency, and has the same genetic origin as that of a subject to which the cell is administered, thus causing reduced occurrence of side effects and exhibiting the same effects as or superior effects to those of bone marrow-derived mesenchymal stem cells or adipose-derived mesenchymal stem cells, and accordingly, the nasal inferior turbinate-derived mesenchymal stem cells can be usefully used in individually customized immunocompatible rheumatoid arthritis prevention or treatment.

BEST MODE

The inventors of the present invention confirmed that human nasal inferior turbinate-derived mesenchymal stem cells were effective in the prevention or treatment of rheumatoid arthritis in a collagen-induced arthritis animal model. Therefore, the present invention provides a pharmaceutical composition for preventing or treating rheumatoid arthritis and a stem cell therapeutic agent for treating rheumatoid arthritis, each including nasal inferior turbinate-derived mesenchymal stem cells as an active ingredient.

Hereinafter, the present invention will be described in detail.

The present invention provides a pharmaceutical composition for preventing or treating rheumatoid arthritis, which includes nasal inferior turbinate-derived mesenchymal stem cells as an active ingredient.

In one embodiment of the present invention, human nasal inferior turbinate-derived mesenchymal stem cells may be isolated from nasal inferior turbinate tissue obtained during a human nasal inferior turbinectomy procedure (see Example 1-1).

In the present invention, the rheumatoid arthritis may be collagen-induced arthritis.

Figure 5:
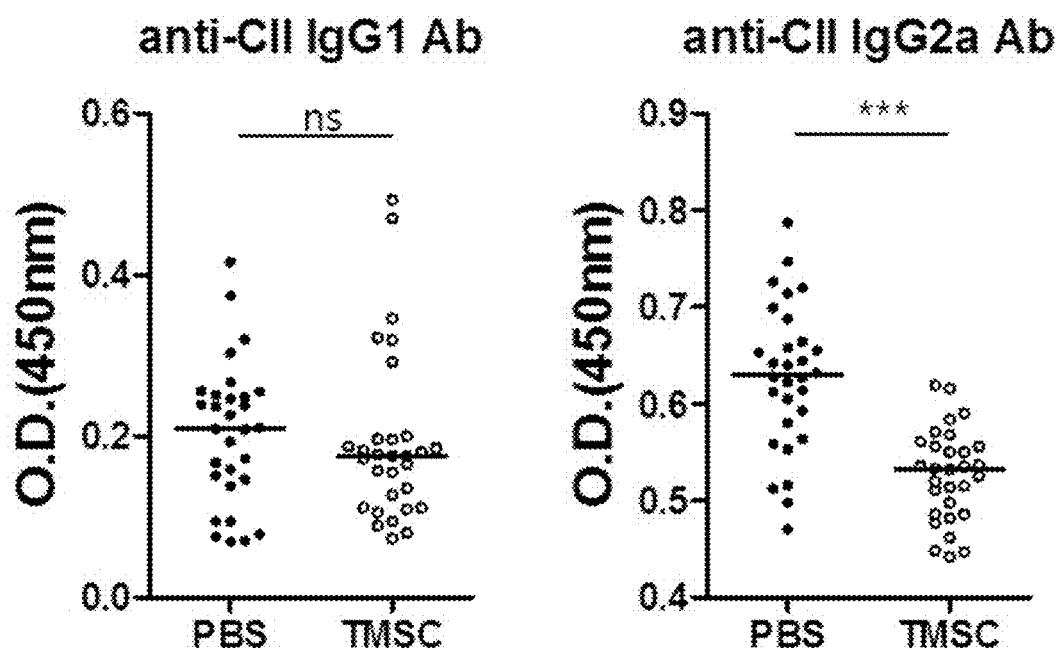
FIG. 5 is a graph showing the results of measuring and comparing the concentrations of collagen antigen-specific autoantibodies in serum according to administration of the control (PBS) and administration of nasal inferior turbinate-derived mesenchymal stem cells (TMSC) in a collagen-induced arthritis animal model.

In another embodiment of the present invention, as a result of measuring immunoglobulin G1 (IgG1) and immunoglobulin G2a (IgG2a), which are inflammation-related factors, in a collagen-induced arthritis animal model in order to compare the concentrations of collagen antigen-specific autoantibodies in serum according to the administration of nasal inferior turbinate-derived mesenchymal stem cells, it was confirmed that the nasal inferior turbinate-derived mesenchymal stem cells significantly reduced IgG2a, which is an inflammation-inducing factor (see FIG. 5 and Example 5).

Figure 8:
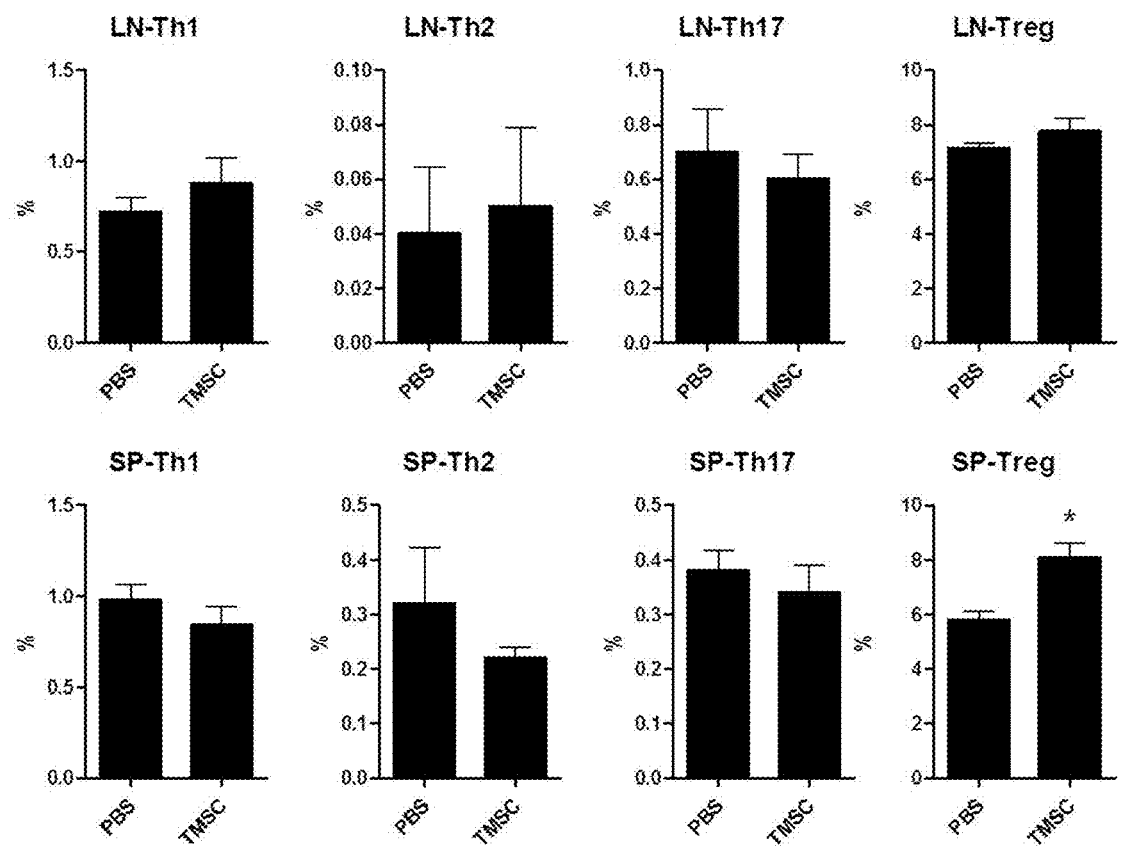
FIG. 8 illustrates the results of measuring and comparing the distribution of inflammatory T-helper cell subtypes and regulatory T-cells in lymph node (LN) and spleen cells (SP) according to administration of the control (PBS) and administration of nasal inferior turbinate-derived mesenchymal stem cells (TMSC) in a collagen-induced arthritis animal model.

In another embodiment of the present invention, as a result of measuring LN-Th1, LN-Th2, LN-Th17A, LN-Treg, SP-Th1, SP-Th2, SP-Th17A, and SP-Treg in a collagen-induced arthritis animal model to compare the distribution of inflammatory T helper cell (Th) subtypes and regulatory T cells (Treg, CD4+CD25+foxp3+ cell) in lymph node (LN) and spleen (SP) cells of mice according to the administration of nasal inferior turbinate-derived mesenchymal stem cells, it was confirmed that the nasal inferior turbinate-derived mesenchymal stem cells significantly increased regulatory T cells (SP-Treg) contributing to immune tolerance among spleen cells (see FIG. 8 and Example 8).

Figure 9:
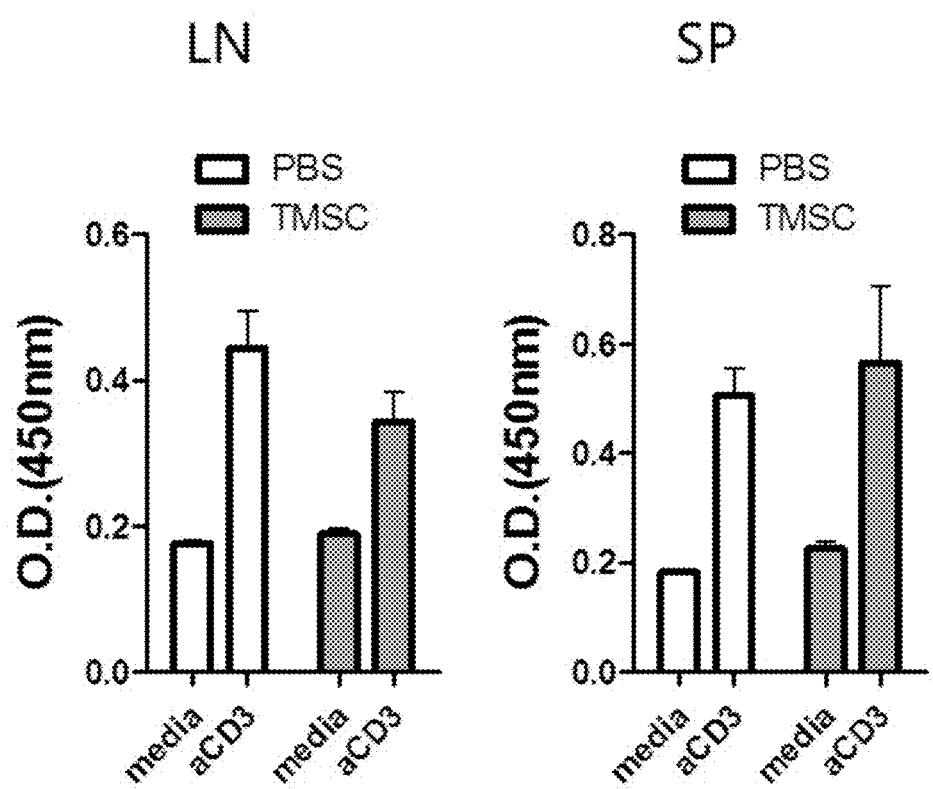
FIG. 9 illustrates the results of measuring and comparing the proliferative abilities of lymph node (LN) and spleen (SP) T cells according to administration of the control (PBS) and administration of nasal inferior turbinate-derived mesenchymal stem cells (TMSC) in a collagen-induced arthritis animal model.

In another embodiment of the present invention, as a result of measuring the proliferative abilities of lymph node and spleen T cells of mice according to the administration of nasal inferior turbinate-derived mesenchymal stem cells in a collagen-induced arthritis animal model, it was confirmed that the nasal inferior turbinate-derived mesenchymal stem cells were unable to reduce the proliferative ability of spleen T cells, but they reduced the proliferative ability of lymph node T cells (see FIG. 9 and Example 9). A buffer used in the present invention may be, but is not limited to, an IC fixation buffer (manufactured by eBioscience) or a Foxp3 fixation/permeabilization buffer (manufactured by eBioscience).

Figure 10:
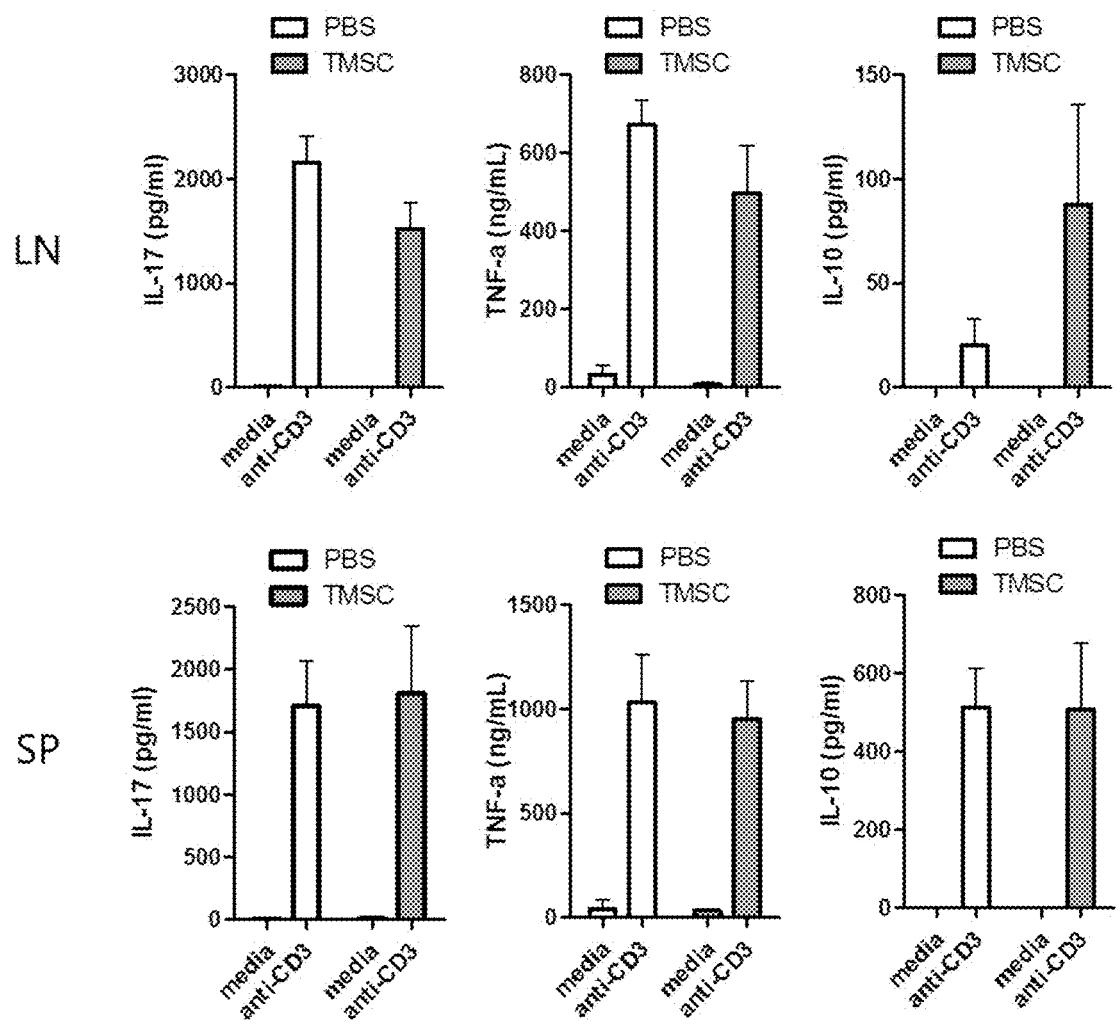
FIG. 10 illustrates the results of measuring and comparing the production abilities of inflammatory and anti-inflammatory cytokines of lymph node (LN) and spleen (SP) T cells according to administration of the control (PBS) and administration of nasal inferior turbinate-derived mesenchymal stem cells (TMSC) in a collagen-induced arthritis animal model.

In another embodiment of the present invention, as a result of comparing the production abilities of inflammatory and anti-inflammatory cytokines of lymph node and spleen T cells of mice according to the administration of nasal inferior turbinate-derived mesenchymal stem cells in a collagen-induced arthritis animal model, it was confirmed that the nasal inferior turbinate-derived mesenchymal stem cells reduced interleukin-17A and tumor necrosis factor-α and increased interleukin-10 (see FIG. 10 and Example 10).

The term "stem cells" as used herein refers to cells that are the foundation of cells or tissues constituting an individual, and have characteristics such as self-renewal by repeatedly dividing, and multipotency which is an ability to differentiate into cells having a specific function according to an environment. Stem cells are generated in all tissues during fetal developmental processes, and found in some tissues in which cells are actively replaced, such as bone marrow, epithelial tissues, and the like in adults. Stem cells are divided into totipotent stem cells that are formed when a first division of a zygote starts, pluripotent stem cells in an inner membrane of the blastocyst that is formed by repeated divisions of the cells, and multipotent stem cells included in mature tissues and organs, according to the type of cells that can be differentiated. In this case, the multipotent stem cells are cells that can be differentiated only into cells specific to tissues and organs including the cells, and are involved in growth and development of tissues and organs of the fetal stage, neonatal stage, and adult stage, homeostatic maintenance of adult tissues, and functions of inducing regeneration when tissues are damaged. Such tissue-specific multipotent cells are collectively referred to as adult stem cells.

Mesenchymal stem cells, which are classified as adult stem cells, are drawing attention as a material for regenerative medicine and can be collected from tissues such as bone marrow, cord blood, and the umbilical cord, and unlike blood stem cells, have the ability to differentiate into cells constituting various human tissues such as adipose tissue cells, bone cells, chondrocytes, neurons, cardiomyocytes, and the like. In the present invention, mesenchymal stem cells isolated from human nasal inferior turbinate tissue were used.

Among adult mesenchymal stem cells, bone marrow-derived mesenchymal stem cells and adipose tissue-derived mesenchymal stem cells are accompanied by severe pain due to a surgery for acquisition thereof which is time-consuming, and the amount of acquired mesenchymal stem cells is very small and a process of clinically culturing a sufficient amount thereof is time-consuming and cost-consuming, and there are high risks such as infection and cell loss. In addition, umbilical cord blood-derived mesenchymal stem cells are difficult to obtain at the time in need thereof and have a problem of long-term storage.

In contrast, human nasal inferior turbinate-derived mesenchymal stem cells are advantageous in that much less bleeding and pain occur during a surgery for the acquisition thereof which is less time-consuming, and mesenchymal stem cells may be continuously obtained through recycling of mesenchymal stem cells isolated from nasal inferior turbinate tissues discarded during nasal inferior turbinate surgery (rhinitis surgery), which is most frequently performed in the otolaryngology field, and has higher proliferative ability than that of the bone marrow-derived mesenchymal stem cells and adipose tissue-derived mesenchymal stem cells. Table 1 below shows data for analysis of human nasal inferior turbinate-derived mesenchymal stem cells, bone marrow-derived mesenchymal stem cells, and adipose tissue-derived mesenchymal stem cells in terms of the risk of surgery for the isolation thereof, the frequency of a surgery enabling stem cell isolation, and the like.

TABLE 1

|  | Human nasal inferior turbinate-derived mesenchymal stem cells | Bone marrow-derived mesenchymal stem cells | Adipose tissue-derived mesenchymal stem cells |
| --- | --- | --- | --- |
| Risk of surgery for stem cell isolation | very low | high | high |
| Frequency of surgery enabling stem cell isolation | very high | low | high |
| Recycling after surgery of discarded tissue for the purpose other than stem cell isolation | very high | low | high |
| Time taken for surgery | 5 minutes to 10 minutes | 1 hour | 3 hours to 4 hours |
| Recovery period after surgery (possibility of daily activities) | within several hours | 3 weeks | within week |
| Bleeding during surgery | below 10 cc | 500 cc to 1,000 cc | 100 cc to 500 cc |
| Volume of tissue acquired during surgery | small | large | large |
| Number of stem cells isolated per unit tissue | $6.55 \times 10^3$ cells/mg | \multicolumn{2}{c}{0.2 to $0.29 \times 10^3$ cells/mg (bone marrow- and adipose tissue-derived stem cells showed similar results)} |
| Proliferative ability of stem cells (P 1 -> P 2) | about 10 times | \multicolumn{2}{c}{about two times (bone marrow- and adipose tissue-derived stem cells showed similar results)} |

This demonstrates that, since human nasal inferior turbinate-derived mesenchymal stem cells can be obtained in a sufficient amount using a safer method at a desired time, compared to existing mesenchymal stem cells, these cells may be usefully used to prevent or treat rheumatoid arthritis with high efficiency. In addition, the nasal inferior turbinate-derived mesenchymal stem cells have the same genetic origin as that of a subject administered therewith, thus causing reduced occurrence of side effects, and may be usefully used in individually customized immunocompatible rheumatoid arthritis prevention or treatment. As used herein, the term "cell therapeutic agent" is a cell and tissue prepared by isolation from a human, culture, and specific manipulation, and is a medicine used for the purpose of treatment, diagnosis, and prevention, and refers to a pharmaceutical product used for the purpose of treatment, diagnosis, and prevention, obtained through a series of actions, including growing and screening allogenic or xenogenic cells in vitro in order to restore the function of the cells or tissues or changing the biological characteristics of cells by any other methods. Cell therapeutic agents are broadly classified into a somatic cell therapeutic agent and a stem cell therapeutic agent according to the degree of differentiation of cells, and the present invention particularly relates to a stem cell therapeutic agent.

The term "prevention" as used herein means all actions that inhibit or delay the onset of rheumatoid arthritis via administration of the composition according to the present invention.

The term "treatment" as used herein means all actions that alleviate or beneficially change symptoms of rheumatoid arthritis via administration of the composition according to the present invention.

The pharmaceutical composition according to the present invention may further include a pharmaceutically acceptable carrier, in addition to the active ingredient. Examples of the pharmaceutically acceptable carrier included in the pharmaceutical composition according to the present invention include, but are not limited to, saline, buffered saline, water, glycerol, polyethylene glycol, vegetable oil, isopropyl myristate, and ethanol, and any suitable preparation known in the art may be used.

A suitable dose of the pharmaceutical composition according to the present invention varies depending on the condition and body weight of a patient, the severity of the disease, dosage form, administration route, and administration period, but may be appropriately selected by those of ordinary skill in the art. The pharmaceutical composition according to the present invention may be administered as an individual therapeutic agent or administered in combination with other therapeutic agents, may be administered sequentially or simultaneously in combination with conventional therapeutic agents, and may be administered in a single dose or multiple doses. It is important to administer the pharmaceutical composition in the minimum amount that enables achievement of the maximum effects without side effects in consideration of all the above-described factors, and this may be easily determined by those of ordinary skill in the art to which the present invention pertains.

In particular, an effective amount of the pharmaceutical composition according to the present invention may vary depending on the age, gender, and body weight of a patient, and generally, the pharmaceutical composition may be administered in an amount of 0.001 mg to 150 mg, preferably, 0.01 mg to 100 mg, per 1 kg body weight daily or every other day, and may be administered once to three times a day. However, the dosage may be increased or decreased according to administration route, the severity of obesity, gender, body weight, age, and the like, and thus the dosage is not intended to limit the scope of the present invention in any way.

The pharmaceutical composition according to the present invention may be administered to a mammal such as a mouse, a rat, livestock, or a human via various routes. The administration method is not particularly limited, and the pharmaceutical composition may be administered via, for example, oral administration, rectal or intravenous injection, muscular injection, subcutaneous injection, intrauterine epidural injection, or intracerebroventricular injection.

Hereinafter, exemplary examples will be described to aid in the understanding of the present invention. However, the following examples are provided only to facilitate the understanding of the present invention and are not intended to limit the scope of the present invention.

Mode of the Invention

Example 1

Materials and Methods 1-1. Culture of Nasal Inferior Turbinate-Derived Mesenchymal Stem Cells Nasal inferior turbinate tissues used in this study were obtained during a nasal inferior turbinectomy procedure and were used with the consent of patients before surgery. Immediately after collecting the nasal inferior turbinate tissues, fibroblasts were isolated by washing 3-5 times with saline containing gentamicin (Kukje Pharma Co., Ltd., Seongnam, Korea).

For the isolation of human nasal inferior turbinate-derived mesenchymal stem cells, surgically removed nasal inferior turbinate tissues were refrigerated at 4° C., and washed three times with an antibiotic-antifungal solution (Gibco, Gaithersburg, Md.) at room temperature. The tissues were washed again three times with neutral phosphate-buffered saline (PBS), and then finely cut into a size of 1 mm$^3$ using small surgical scissors.

The nasal inferior turbinate-derived mesenchymal stem cells were placed in a 100 mm culture dish, and the dish was covered with sterilized slide glass to attach the cells to the culture dish, and Dulbecco's Modified Eagle's Media (DMEM) containing 10% fetal bovine serum (FBS) was added thereto, followed by incubation at 37□ in a 5% $CO_2$ incubator. After 2 to 3 weeks of culture, the slide glass was removed, and cells floating in the culture solution were removed by washing, and human nasal inferior turbinate-derived mesenchymal stem cells that had been attached to the bottom of the culture dish were detached using trypsin and cultured to the third passage for use.

Figure 1:
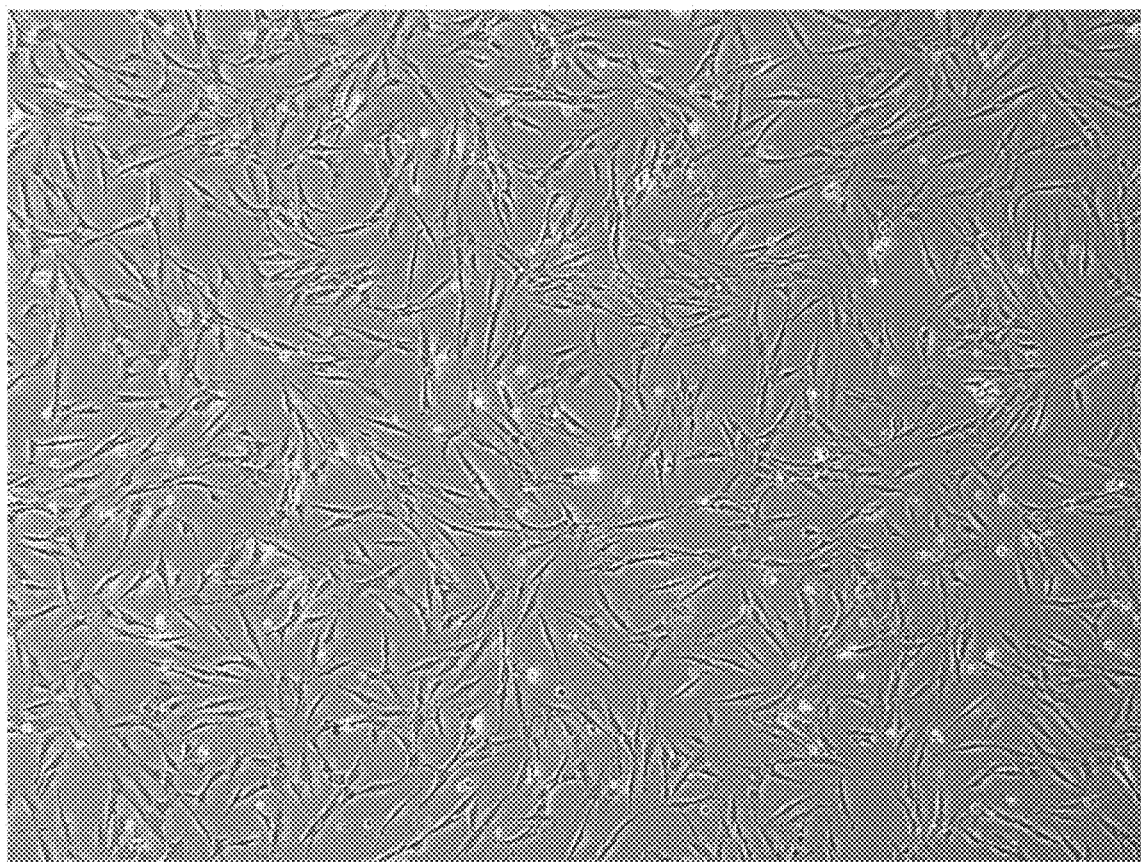
FIG. 1 is a view illustrating the morphological analysis of human nasal inferior turbinate stem cells.

As a result, as shown in FIG. 1, microscopic findings on the cells obtained using the method all showed similar shapes in the form of fusiform fibroblasts.

1-2. Establishment of Collagen-Induced Arthritis and Administration of Nasal Inferior Turbinate-Derived Mesenchymal Stem Cells (TMSC)

Seven-week-old male DBA1/J (produced by JAX™) mice were used for the experiment after being adapted to the environment of an animal laboratory for one week. The conditions of an animal breeding room were 22.0±2□, illuminated with 200 to 300 Lux for 12 hours during the day, and light was totally shielded for 12 hours. 100 μg of type II collagen (Chondrex) and complete Freund's adjuvant (CFA; manufactured by Chondrex) were mixed in a ratio of 1:1 (w/v), the mixture was intradermally injected into the tail of each DBA1/J mouse to induce a primary immune response. After 2 weeks, 100 μg of type II collagen and incomplete Freund's adjuvant were mixed in a ratio of 1:1 (v/v), and the mixture was subcutaneously injected into the sole of one hind limb to induce a secondary immune response. Between 5 weeks and 6 weeks after the injection for primary immunization, the nasal inferior turbinate-derived mesenchymal stem cells were prepared at a density of $1×10^6$ cells/100 μl/mouse and injected into the tail vein of each mouse three times, and as a control, 100 μl/mouse of phosphate-buffered saline (PBS) was injected into the same site.

1-3. Evaluation of Arthritis

After confirming that the onset of arthritis was progressing from erythema slowly appearing 14 days after the injection for primary immunization, cages were redistributed to match a mean arthritis index for each group, and then PBS was used as a control, and nasal inferior turbinate-derived mesenchymal stem cells were injected into an experimental group.

Visual observation of arthritis lesions was performed using the following scores based on the references (Barnett M L, Kremer J M, St Clair E W, Clegg D O, Furst D, Weisman M, et al. Treatment of rheumatoid arthritis with oral type II collagen. Results of a multicenter, double-blind, placebo-controlled trial. Arthritis Rheum 1998; 41: 290-7).

0 points: no edema or swelling, 1 point: mild edema and redness limited to the foot or ankle joint, 2 points: mild edema and redness from the ankle joint to the tarsal bone, 3 points: moderate edema and redness from the ankle joint to the tarsal bone, 4 points: swelling and redness and joint stiffness throughout the limb from the ankle.

Therefore, the highest score for arthritis lesions was 12 points per mouse, excluding the score of the limb injected for secondary immunization, and observation was performed three times a week for up to 11 weeks from the time of the primary immunization injection, and evaluation data was written by three people who were not related to the experiments. The mean arthritis indexes of a PBS-administered group and a TMSC-administered group were compared with each other. In addition, the arthritis index of each mouse was expressed as incidence through the evaluation method. An incidence of 33.3% was given when the arthritis index of one limb among three limbs of a mouse reached 1, an incidence of 66.7% was given when the arthritis indexes of two limbs reached 1, an incidence of 100% was given when all the arthritis indexes of three limbs reached 1, and the arthritis incidences of all mice were averaged.

1-4. Immunoglobulin G Measurement

Serum obtained by orbital blood collection was prepared by diluting 1000-fold at week 11 after the injection for primary immunization. Type II collagen (Chondrex) was diluted to a concentration of 4 μg/ml in a sodium carbonate solution (pH 9.6, manufactured by Sigma), and then 100 μl of the resulting solution was distributed into each well of a 96-well plate (manufactured by Nunc), followed by a coating process in a refrigerator at 4□ for 16 hours. 200 μl of PBS containing 1% bovine serum albumin (manufactured by Amresco) was added to each well and left at room temperature for 30 minutes to inhibit non-specific reactions. 100 μl of the diluted serum was added to each well and a reaction was allowed to occur therebetween at room temperature for 1 hour. After washing 4 times with PBS containing 0.05% Tween 20 (manufactured by Amresco), a horse peroxidaseconjugated anti-mouse IgG1 or IgG2a antibody (Bethyl Laboratories) was added and a reaction was allowed to occur for 1 hour. After 4 washes, 50 μl of a TMB substrate reagent (ebioscience) was added to each well, and then 50 μl of 1 M $H_2SO_4$ was added to each well to stop the reaction. Absorbance values at a wavelength of 450 nm were measured and compared using a microplate reader (manufactured by Molecular Devices).

1-5. Histological Changes in Joints

To observe joint swelling visually, the opposite hind limb on which injection for secondary immunization was not performed, was photographed at the end of the experiment to compare the degrees of joint swelling with the naked eye.

Each group of mice was sacrificed and joint tissues were collected, fixed in a 10% neutral buffered formalin solution for one day, and then decalcified with Calci-Clear Rapid (National Diagnostics) for 7 hours. After washing with tap water, stepwise dehydration with ethanol at a concentration of 70% to 100%, brightening with xylene, embedding with paraffin, cutting the finished limb joint paraffin block into 7 μm thickness, and Hematoxylin-Eosin (H-E) staining were performed.

1-6. Isolation and Stimulation of Lymph Node Cells and Spleen Cells

At the end of the experiment, axillary lymph nodes and inguinal lymph nodes of the sacrificed mice were mixed and chopped in RPMI1640 medium containing 10% FBS to prepare single cells. Spleen tissue was prepared in single-cell units in the same manner as lymph nodes, and then a reaction was allowed to occur in a lysis solution (2.06% tris-(hydroxymethyl)-aminomethane (Tris) and 0.83% $NH_4Cl$ were mixed in a ratio of 1:9) for 5 minutes for hemolysis of red blood cells. After the reaction, spleen cells were obtained by filtration with a 40 μm cell strainer (manufactured by BD Falcon). Respective cells were dispensed into 24-well plates at a density of $1 \times 10^6$ cells/well using RPMI1640 (manufactured by Gibco) medium containing 10% FBS.

1-7. Flow Cytometry

Among the lymph node cells and spleen cells prepared in single-cell units, the remainder in wells except for regulatory T cell assay wells was stimulated in 25 ng/ml of phorbol 12-myristate 13-acetate (PMA, manufactured by Sigma) and 250 ng/ml of ionomycin in a 37° C. incubator for a total of 4 hours. At this time, stimulation was performed together with Golgistop (manufactured by BD) to inhibit protein secretion, thereby allowing proteins to be accumulated in cells. After completion of the reaction, the cells were collected in a tube and washed with PBS containing 0.5% bovine serum albumin (BSA), followed by fluorescent staining with an anti-CD3 PerCP-Cy5.5 antibody, an anti-CD4 Pacific Blue antibody, and an anti-CD25 APC antibody (all manufactured by BioLegend) for 30 minutes. After washing, T helper cells (Th1, Th2, Th17A cells) were reacted in IC fixation buffer (manufactured by eBioscience), and regulatory T cells were reacted in Foxp3 fixation/permeabilization buffer (manufactured by eBioscience), and then washed with a permeabilization buffer (manufactured by eBioscience) solution. To stain inflammatory cells (Th1, $CD3^+CD4^+$ IFN gamma (γ)+ cells; Th2, $CD3^+CD4^+IL-4^+$ cells; Th17A, $CD3^+CD4^+IL-17A^+$ cells), an Alexa488-labeled anti-IL-17A antibody (manufactured by ebioscience), an APC-labeled anti-IFNγ antibody (manufactured by BD), and an APC-labeled anti-IL-4 antibody (manufactured by BD) were used, and a PE-labeled anti-foxp3 antibody (manufactured by eBioscience) was used to stain regulatory T cells ($CD4^+CD25^+foxp3^+$ cells), followed by a reaction for 30 minutes, washing, and analysis, and the used equipment was BD LSRII Fortessa.

1-8. Observation of Proliferative Abilities of Lymph Node and Spleen T Cells

Lymph node (LN) and spleen (SP) cells were dispensed into a 96-well plate (manufactured by Thermo) at a density of $2 \times 10^5$ cells/well and stimulated with 0.5 μg/ml of a plate-bound anti-CD3e monoclonal antibody (manufactured by BD) for 2 days. Two hours before the end of the reaction, 10 μl of a CCK-8 reagent (manufactured by Dojindo) was dispensed into each well, and absorbance values at 450 nm were measured using a microplate reader (manufactured by Molecular Devices) at the end of the reaction.

1-9. Cytokine Production Observation

Lymph node and spleen cells were dispensed into a 24-well plate (manufactured by Eppendorf) at a density of $1 \times 10^6$ cells/well and stimulated with 0.5 μg/ml of a plate-bound anti-CD3e monoclonal antibody (manufactured by BD) for 2 days to allow a reaction to occur, and a supernatant obtained after the reaction was completed was refrigerated and used for analysis. Each of a monoclonal anti-IL-17A antibody, an anti-TNFα antibody, and an anti-IL-10 antibody (all manufactured by R&D Systems) was diluted in a sodium carbonate solution (pH 9.6) and a reaction was allowed to occur therebetween in a 4° C. refrigerator for 16 hours. 200 μl of PBS containing 1% BSA (manufactured by Amresco) was added to each well and kept at room temperature for 2 hours to inhibit non-specific reactions. 100 μl of the collected culture supernatant was added to each well and a reaction was allowed to occur therebetween at room temperature for 2 hours. At this time, recombinant IL-17A, TNF-α, and IL-10 proteins (manufactured by R&D Systems) were subjected to serial dilution and used as references. The reaction product was washed four times with PBS containing 0.05% Tween 20 (manufactured by Amresco), followed by reaction with a biotin-attached anti-mouse IL-17A antibody, anti-TNFα antibody, and anti-IL-10 antibody (manufactured by R&D Systems) at room temperature for 2 hours and washing four times. Thereafter, an Extravidin-HRP (manufactured by Sigma) solution was diluted at a ratio of 1:4000, 50 μl of the solution was dispensed into each well, a reaction was allowed to occur therebetween at room temperature for 2 hours, followed by washing four times, and then 50 μl of a TMB substrate reagent (manufactured by ebioscience) and 50 μl of 1 M $H_2SO_4$ were sequentially added to each well to stop the reaction. At the completion of the reaction, absorbance values at 450 nm were measured using a microplate reader.

1-10. Observation of Effect of Nasal Inferior Turbinate-Derived Mesenchymal Stem Cells (TMSC) on Inhibiting the Proliferation of Healthy Human T Cells 20 cc of blood was collected from healthy volunteers, and then diluted in a 1:1 ratio with PBS. This was slowly flowed into a 50 ml tube containing 10 ml of Ficoll-Hypaque (manufactured by GE Healthcare), floated to the upper layer, and centrifuged at room temperature and 2,000 rpm for 20 minutes. A buffy coat layer present between a Ficoll layer and a plasma layer was separately collected to isolate peripheral blood mononuclear cells (PBMC) therefrom. The cells were washed with PBS, washed once again with PBS containing 3% fetal bovine serum and 10 mM EDTA and centrifuged. Peripheral blood mononuclear cells were released without clumping, and then $CD4^+T$ cells were isolated using a Magnisort Human $CD4^+T$ cell enrichment kit (manufactured by eBioscience) (The isolation method was in accordance with the manufacturer's recommendation). CD4+T cells were labeled with CD25 microbeads (manufactured by Miltenyi Biotec), and then CD4+CD25−T cells were isolated and labeled with a Cell trace violet dye (Thermo) at 1:1000 for 20 minutes at 37° C. The labeled CD4+CD25−T cells ($5 \times 10^4$ cells per well) were activated with anti-CD3 and anti-CD28 Dynabeads (manufactured by Invitrogen) at a ratio of 1:1. At this time, T cells and nasal inferior turbinate-derived mesenchymal stem cells, bone marrow-derived mesenchymal stem cells, or adipose-derived mesenchymal stem cells were co-cultured in a ratio of 5:1 to 2:1. To confirm whether IDO is involved in the inhibition of T cell proliferation, 1-methyl-L-tryptophan, which is a substrate analog of the IDO enzyme, was added at a concentration of 100 nM to the co-culture conditions of T cells and TMSC. After 6 days, the cells were collected in a 5 ml tube, washed once with PBS containing 0.5% BSA, and then the cell trace violet dye-labeled CD4+CD25−T cells were analyzed through flow cytometry equipment as the frequency of cells exhibiting reduced fluorescence sensitivity at wavelengths of excitation 401 nm/emission 452 nm.

1-11. Analysis of Indoleamine-2,3-dioxygenase (IDO) mRNA of Nasal Inferior Turbinate-Derived Mesenchymal Stem Cells (TMSC) Co-Cultured with T Cells After completion of the co-culture, adherent cells, which were regarded as nasal inferior turbinate-derived mesenchymal stem cells, were treated with 1 ml of RNA iso (manufactured by Takara) to extract total RNA therefrom. The extraction method was in accordance with the manufacturer's recommendation. The extracted RNA was quantified using Nanodrop equipment, and then 2 μg of RNA was reverse transcribed into cDNA using a Transcriptor first strand cDNA synthesis kit (Roche). 1 μl of cDNA was placed in a 0.2 ml tube and 1 pmole of an IDO forward primer (SEQ ID NO: 1): 5'-GCC AAC TCT CCA AGA AAC TG-3', 1 pmole of an IDO reverse primer (SEQ ID NO: 2): 5'-GCA GTC TCC ATC ACG AAA TG-3', 10 μl of SYBR Green I Master (Roche), and 8 μl of nuclease-free water (manufactured by Roche) were mixed therewith, and real-time amplification was performed under a 60° C. annealing condition using LightCycler96 equipment (manufactured by Roche). For the relative quantification of IDO mRNA, the beta-actin gene was amplified in the same manner, and the primers used were as follows: Beta-actin forward primer (SEQ ID NO: 3): 5'-GGA CTT CGA GCA AGA GAT GG-3; and 1 pmole of a beta-actin reverse primer (SEQ ID NO: 4): 5'-TGT GTT GGG GTA CAG GTC TTT G-3'. The relative quantification was performed using an existing general method, wherein a Cq level was obtained by automatically calculating the time at which the mRNA concentration started to be amplified, a delta Cq value was obtained by subtracting the Cq value of beta-actin from the Cq level, and a delta delta Cq (ddCq) value was obtained by subtracting a Cq value obtained under the remaining co-culture condition from the obtained delta Cq (dCq) value. The value was converted into a $2^{-ddCq}$ value for comparison.

Example 2

Figure 2:
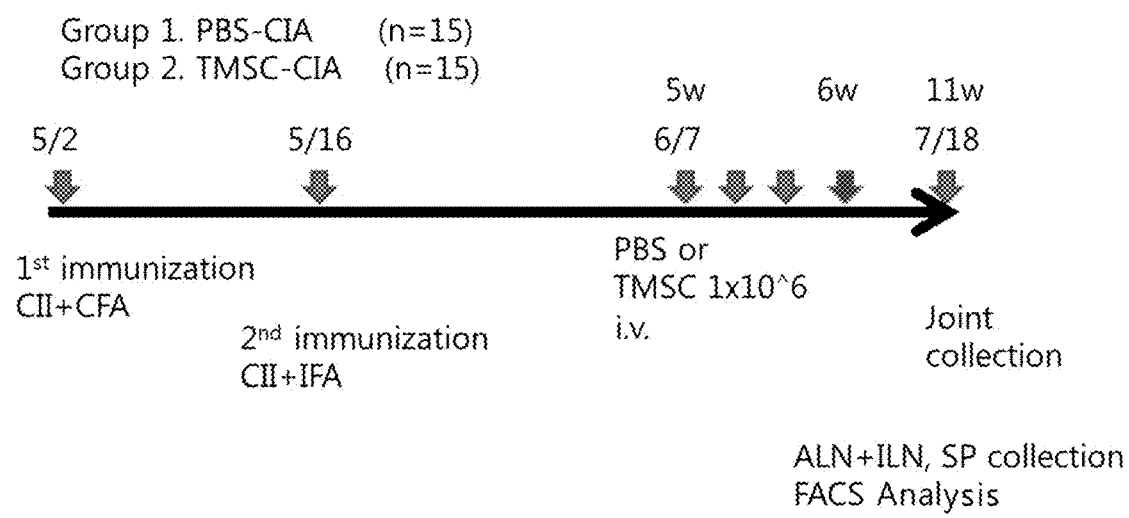
FIG. 2 illustrates collagen-induced arthritis animal modeling and the administration time of nasal inferior turbinate-derived mesenchymal stem cells.

Preparation of Collagen-Induced Arthritis Animal Modeling and Administration of Nasal Inferior Turbinate-Derived Mesenchymal Stem Cells As shown in FIG. 2, 100 μg of bovine type II collagen and complete Freund's adjuvant were mixed in a ratio of 1:1 (w/v), the mixture was intradermally injected into the tail of each 8-week-old male DBA1/J mouse to induce a primary immune response, and after 2 weeks, 100 μg of bovine type II collagen and incomplete Freund's adjuvant were mixed in a ratio of 1:1 (v/v), and the mixture was subcutaneously injected into the sole of one paw to induce a secondary immune response.

Between 5 weeks and 6 weeks after the injection for primary immunization, human nasal inferior turbinate-derived mesenchymal stem cells were injected at a density of $1 \times 10^6$ cells into the tail vein of each mouse three times, and as a control, 100 μl of PBS was injected into each mouse, and the arthritis index was observed further for 5 weeks up to week 11.

Example 3

Comparison of Arthritis Index According to Administration of Nasal Inferior Turbinate-Derived Mesenchymal Stem Cells in Collagen-Induced Arthritis Animal Model To determine whether the arthritis index is affected by the administration of nasal inferior turbinate-derived mesenchymal stem cells, scores for the arthritis index were measured according to Example 1-3. All data are expressed as mean±SEM (*** $P<0.001$).

Figure 3:
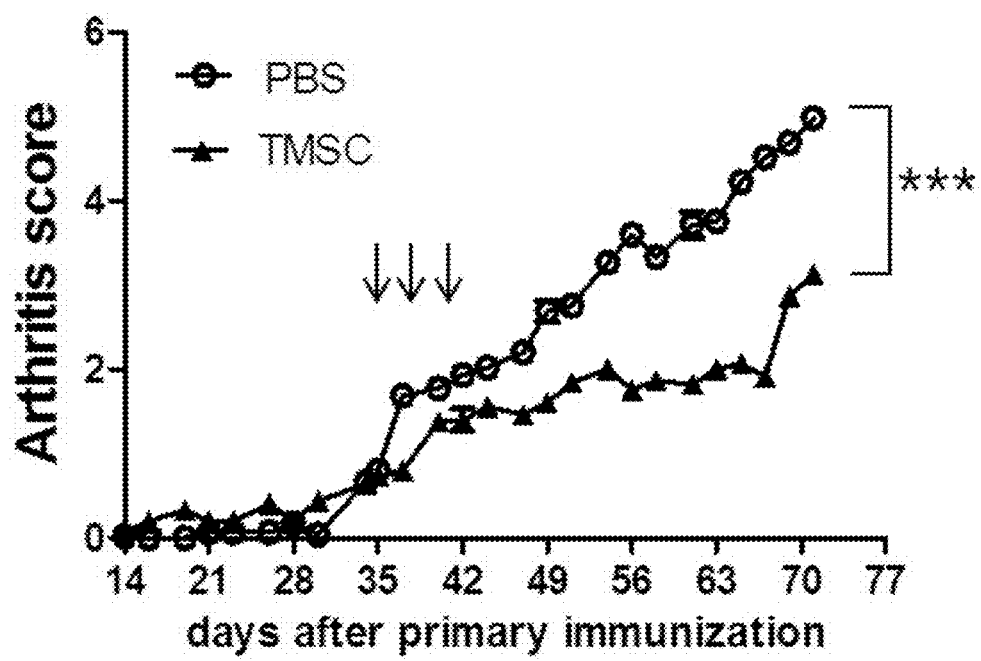
FIG. 3 is a graph showing the results of measuring and comparing arthritis indexes according to administration of the control (PBS) and administration of nasal inferior turbinate-derived mesenchymal stem cells (TMSC) in a collagen-induced arthritis animal model.

As a result, as shown in FIG. 3, the onset of arthritis continued slowly until the end of the experiment after the first injection of nasal inferior turbinate-derived mesenchymal stem cells, performed on day 35 after the injection for primary immunization, which was significantly different from the control.

Example 4

Comparison of Arthritis Incidence According to Administration of Nasal Inferior Turbinate-Derived Mesenchymal Stem Cells in Collagen-Induced Arthritis Animal Model To determine whether arthritis incidence is affected by the administration of nasal inferior turbinate-derived mesenchymal stem cells, the arthritis incidence was measured according to Example 1-3. All data are expressed as mean±SEM (*** $P<0.001$).

Figure 4:
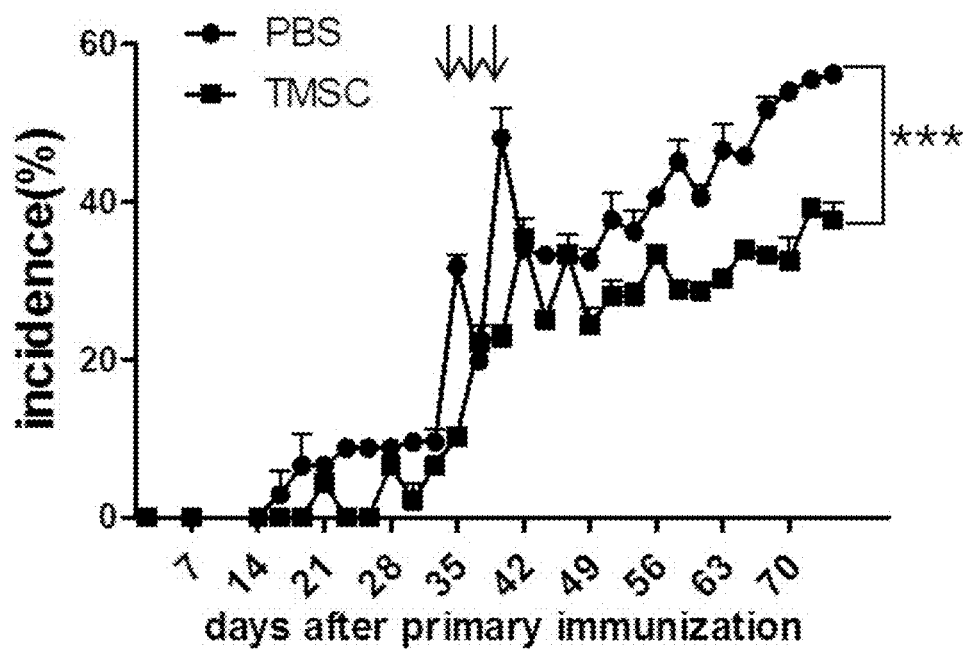
FIG. 4 is a graph showing the results of measuring and comparing the incidence of arthritis according to administration of the control (PBS) and administration of nasal inferior turbinate-derived mesenchymal stem cells (TMSC) in a collagen-induced arthritis animal model.

As a result, as shown in FIG. 4, it was confirmed that the incidence of arthritis was slowed by the administration of nasal inferior turbinate-derived mesenchymal stem cells from day 49 after the injection for primary immunization to the end of the experiment.

Example 5

Comparison of Concentrations of Collagen Antigen-Specific Autoantibodies in Serum According to Administration of Nasal Inferior Turbinate-Derived Mesenchymal Stem Cells in Collagen-Induced Arthritis Animal Model To determine whether the concentrations of collagen antigen-specific autoantibodies in the serum of collagen-induced arthritis animal model mice are affected by the administration of nasal inferior turbinate-derived mesenchymal stem cells, immunoglobulin G was measured according to Example 1-4. In mice, IgG1 is known to be an inflammation inhibitor and IgG2a is known to be an inflammation-inducing factor, and all data are expressed as median (*** $P<0.001$).

As a result, as shown in FIG. 5, IgG2a increases in proportion to the arthritis induction time when collagen-induced arthritis (CIA) is induced, and it was confirmed that the concentration of an inflammation-inducing collagen-specific IgG2a antibody was statistically significantly reduced in the serum of mice into which nasal inferior turbinate-derived mesenchymal stem cells were injected, compared to the control.

Example 6

Comparison of Joint Swelling According to Administration of Nasal Inferior Turbinate-Derived Mesenchymal Stem Cells in Collagen-Induced Arthritis Animal Model To determine whether the degree of joint swelling is affected by the administration of nasal inferior turbinate-derived mesenchymal stem cells, the hind limbs of mice of the PBS-administered control and a treatment group administered nasal inferior turbinate-derived mesenchymal stem cells were photographed on day 77 after the injection for primary immunization. A subject for evaluating the incidence of arthritis included only limbs that did not undergo the injection for secondary immunization.

Figure 6:
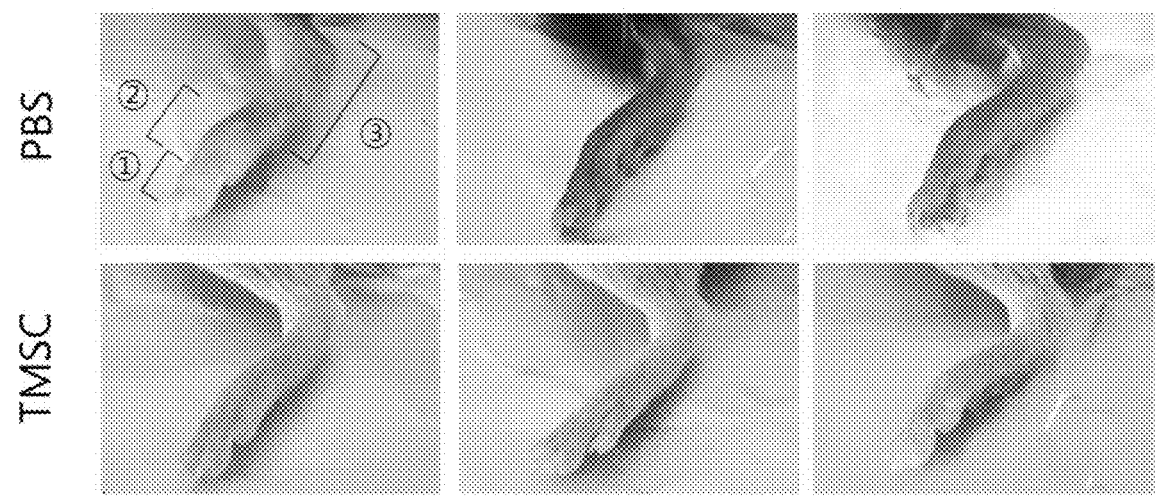
FIG. 6 illustrates the results of comparing the degree of joint swelling according to administration of the control (PBS) and administration of nasal inferior turbinate-derived mesenchymal stem cells (TMSC) in a collagen-induced arthritis animal model.

As a result, as shown in FIG. 6, edema across the phalanx bone (①)—metatarsal bone (②)—tarsal bone (③) was observed in the limbs of the PBS-administered control. In contrast, edema was hardly observed in the phalanx bones of the limbs of mice administered nasal inferior turbinate-derived mesenchymal stem cells, and mild edema was observed in the metatarsal bones compared to the control. It was also confirmed that edema in the tarsal bone side was also reduced.

Example 7

Comparison of Degree of Inflammation Infiltration into Joint Tissue Section According to Administration of Nasal Inferior Turbinate-Derived Mesenchymal Stem Cells in Collagen-Induced Arthritis Animal Model To determine whether the degree of inflammation infiltration into joint tissue sections is affected by the administration of nasal inferior turbinate-derived mesenchymal stem cells, the tissue pathology of the tarsal bones of hind limbs of mice of the control and mice administered nasal inferior turbinate-derived mesenchymal stem cells was photographed.

Figure 7A:
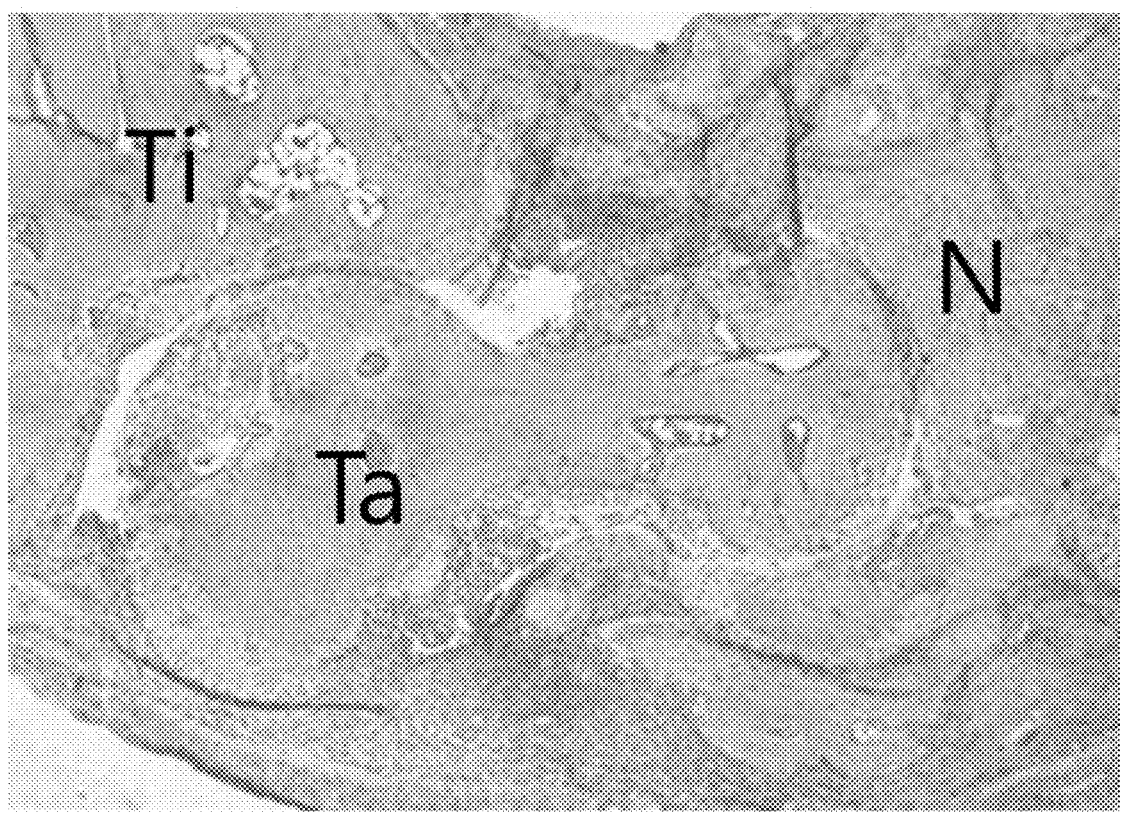
FIG. 7A illustrates the tarsal bone tissue pathology of the control administered PBS in a collagen-induced arthritis animal model.
Figure 7B:
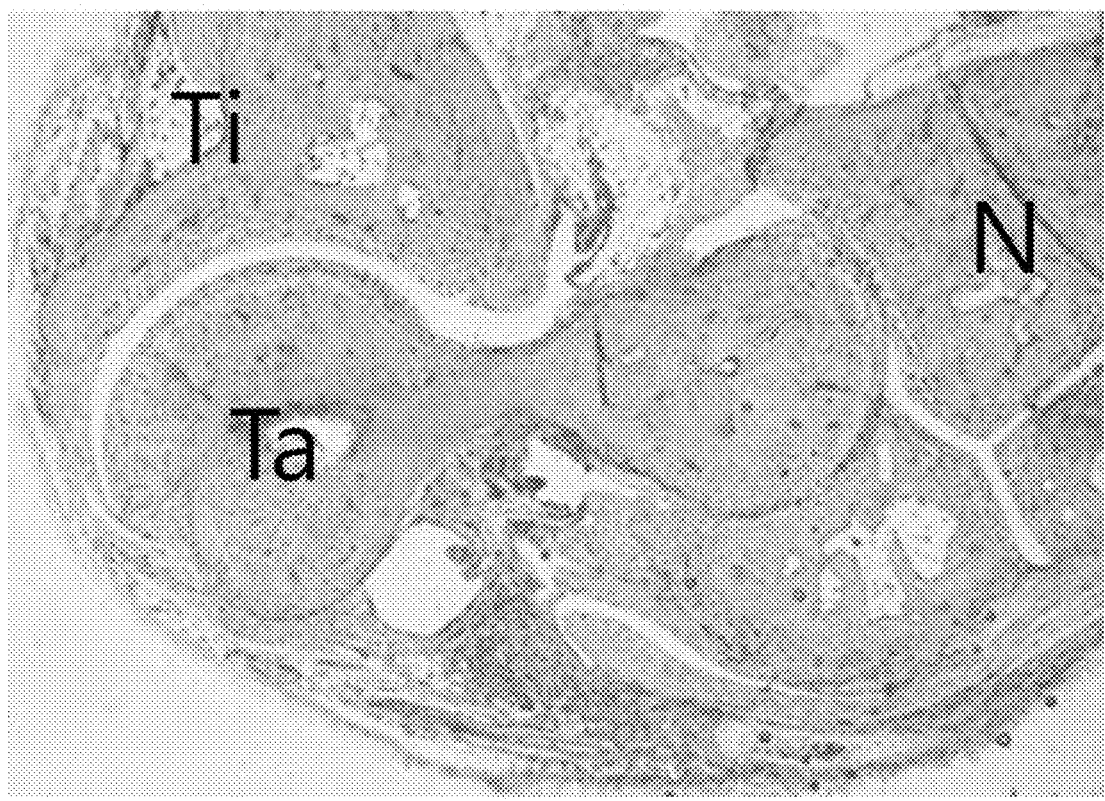
FIG. 7B illustrates the tarsal bone tissue pathology of an experimental group administered nasal inferior turbinate-derived mesenchymal stem cells (TMSC) in a collagen-induced arthritis animal model.

As a result, as illustrated in FIGS. 7A and 7B, it was confirmed that, while inflammatory cells infiltrated around the talus (Ta) bone at the tarsal bone site of a hind limb of each mouse of the control, and thus the pannus structure was destroyed and inflammatory cell infiltration between the talus bone (Ta) and the tibia bone (Ti), between the tibia bone (Ti) and the navicular bone (N), and between the talus bone (Ta) and the navicular bone (N) was observed, the infiltration of inflammatory cells was significantly reduced by the administration of nasal inferior turbinate-derived mesenchymal stem cells.

Example 8

Comparison of Distribution of Inflammatory T Helper Cell Subtypes and Regulatory T Cells in Lymph Node (LN) and Spleen (SP) Cells of Mice According to Administration of Nasal Inferior Turbinate-Derived Mesenchymal Stem Cells in Collagen-Induced Arthritis Animal Model To determine whether the distribution of inflammatory T helper cell subtypes and regulatory T cells in lymph node (LN) and spleen (SP) cells of mice is affected by the administration of nasal inferior turbinate-derived mesenchymal stem cells, lymph node cells and spleen cells were isolated and stimulated according to Example 1-6 to analyze the T cell fraction of each cell type. All data are expressed as mean±SEM (* $P<0.05$).

As a result, as illustrated in FIG. 8, a significant decrease in the fraction of inflammatory cells (Th1, $CD3^+CD4^+IFN\gamma^+$ cells; Th2, $CD3^+CD4^+IL-4^+$ cells; and Th17A, $CD3^+CD4^+IL-17A^+$ cells) in the collective lymph nodes, which are secondary lymphoid organs present in peripheral sites and spleen cells, by administration of nasal inferior turbinate-derived mesenchymal stem cells could not be confirmed, whereas it was confirmed that the fraction of regulatory T cells (Treg, $CD4^+CD25^+foxp3^+$ cells) contributing to immune tolerance among spleen cells was increased.

Example 9

Comparison of Proliferative Abilities of Lymph Node (LN) and Spleen (SP) T Cells of Mice According to Administration of Nasal Inferior Turbinate-Derived Mesenchymal Stem Cells in Collagen-Induced Arthritis Animal Model To determine whether the proliferative abilities of lymph node (LN) and spleen (SP) T cells are affected by the administration of nasal inferior turbinate-derived mesenchymal stem cells, flow cytometry and T cell proliferative capacity were measured according to Examples 1-7 and 1-8.

As a result, as illustrated in FIG. 9, stimulation with an aCD3 antibody selectively acted on T cells with T cell receptors, and the greater the severity of articular edema, the more active the proliferative capacity of peripheral lymph node T cells, and it was confirmed that the proliferative ability of lymph node T cells tended to decrease by the administration of nasal inferior turbinate-derived mesenchymal stem cells, compared to the control, but it was confirmed that there was no difference in proliferative capacity between spleen T cells and the control.

Example 10

Comparison of Abilities of Lymph Node (LN) and Spleen (SP) T Cells to Produce Inflammatory and Anti-Inflammatory Cytokines According to Administration of Nasal Inferior Turbinate-Derived Mesenchymal Stem Cells in Collagen-Induced Arthritis Animal Model To determine whether the abilities of lymph node (LN) and spleen (SP) T cells to produce inflammatory and anti-inflammatory cytokines are affected by the administration of nasal inferior turbinate-derived mesenchymal stem cells, the production of cytokines was observed according to Example 1-9. Interleukin-17A and tumor necrosis factor-α are representative inflammatory cytokines known in arthritis animal models, and interleukin-10 is a cytokine produced in inflammation-inhibitory regulatory T cells in response to inflammatory cytokines.

As a result, as shown in FIG. 10, it was confirmed that the interleukin-17A and tumor necrosis factor-alpha, which are produced when lymph node T cells are stimulated with an aCD3 antibody, tended to decrease by the administration of nasal inferior turbinate-derived mesenchymal stem cells, whereas it was confirmed that the production of inflammation-inhibitory interleukin-10 was increased. In contrast, in the experiment using spleen T cells, a difference in cytokine production ability by the administration of stem cells could not be confirmed.

Example 11

Comparison of Arthritis Indexes and Concentrations of Collagen Antigen-Specific Autoantibodies in Serum According to Mesenchymal Stem Cells Derived from Different Tissue Source in Collagen-Induced Arthritis Animal Model To compare the effects of attenuating arthritis progression when nasal inferior turbinate-derived mesenchymal stem cells and mesenchymal stem cells derived from different tissue source were administered to collagen-induced arthritis animal models, bovine type II collagen and complete Freund's adjuvant were mixed in a ratio of 1:1 (w/v), the mixture was intradermally injected into the tail of each male DBA1/J mouse (n=32) to induce a primary immune response, and after 2 weeks, bovine type II collagen and incomplete Freund's adjuvant were mixed in a ratio of 1:1 (v/v), and the mixture was subcutaneously injected into the sole of one foot to induce a secondary immune response.

5 weeks after the injection for primary immunization, nasal inferior turbinate-derived mesenchymal stem cells (TMSC), bone marrow-derived mesenchymal stem cells (BM-MSC), and adipose-derived mesenchymal stem cells (Ad-MSC) were injected at a density of $1\times10^6$ into the tail vein of each mouse at intervals of two days a total of three times and the arthritis index was observed further for four weeks up to week 9. All results were expressed as mean (±SEM).

The arthritis index was measured by three observers every two to three days a week, and all data are expressed as mean±standard deviation (SD). The serum of mice was collected 9 weeks after the injection for primary immunization, and the serum was diluted 1:1000 or 1:5000 to identify anti-CII IgG1 or anti-CII IgG2a.

Figure 11A:
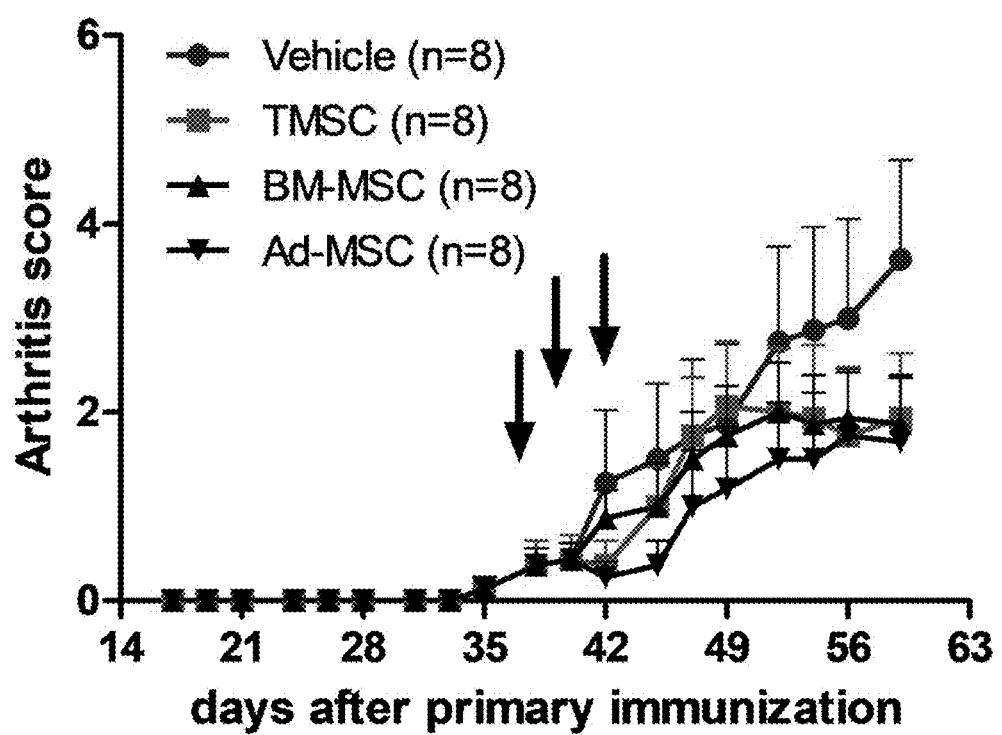
FIG. 11A is a graph showing the results of measuring and comparing arthritis indexes according to administration of nasal inferior turbinate-derived mesenchymal stem cells (TMSC), bone marrow-derived mesenchymal stem cells (BM-MSC), and adipose-derived mesenchymal stem cells (Ad-MSC) in a collagen-induced arthritis animal model.
Figure 11B:
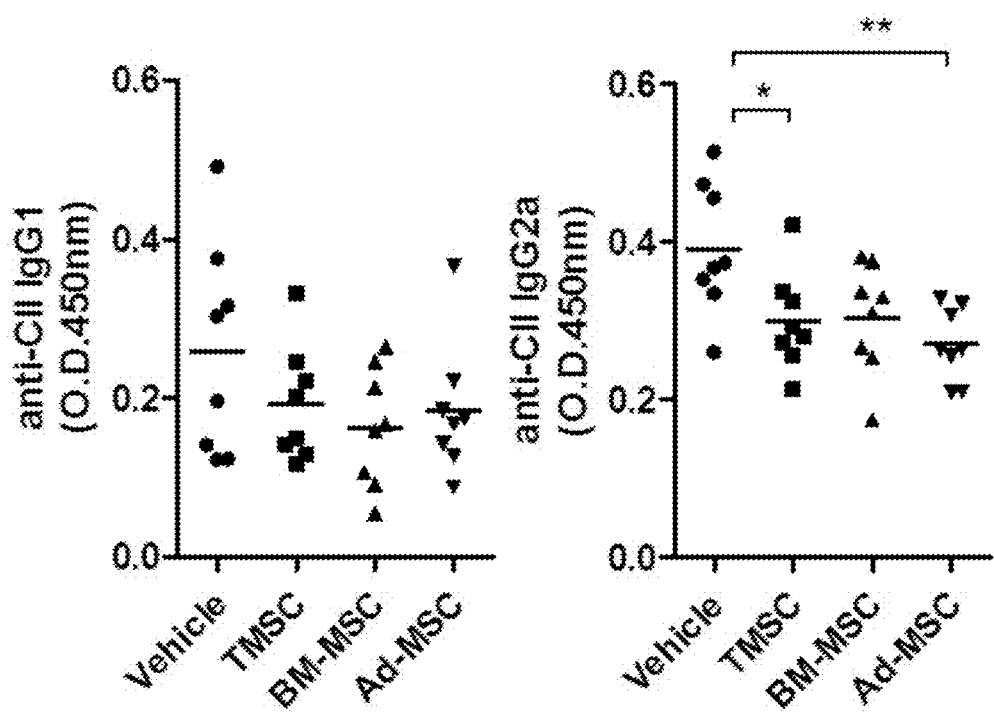
FIG. 11B is a graph showing the results of measuring and comparing the concentrations of collagen antigen-specific autoantibodies according to administration of nasal inferior turbinate-derived mesenchymal stem cells (TMSC), bone marrow-derived mesenchymal stem cells (BM-MSC), and adipose-derived mesenchymal stem cells (Ad-MSC) in a collagen-induced arthritis animal model.

As a result, the arthritis indexes and the levels of inflammation-related factors such as collagen antigen-specific IgG1 and IgG2a were shown to be similar in all groups except for the control, from which it was confirmed that the nasal inferior turbinate-derived mesenchymal stem cells (TMSC), the bone marrow-derived mesenchymal stem cells (BM-MSC), and the adipose-derived mesenchymal stem cells (Ad-MSC) exhibited the same arthritis-inhibitory efficacy (* $P<0.05$; ** $P<0.01$) (see FIGS. 11A and 11B).

Example 12

Figure 12:
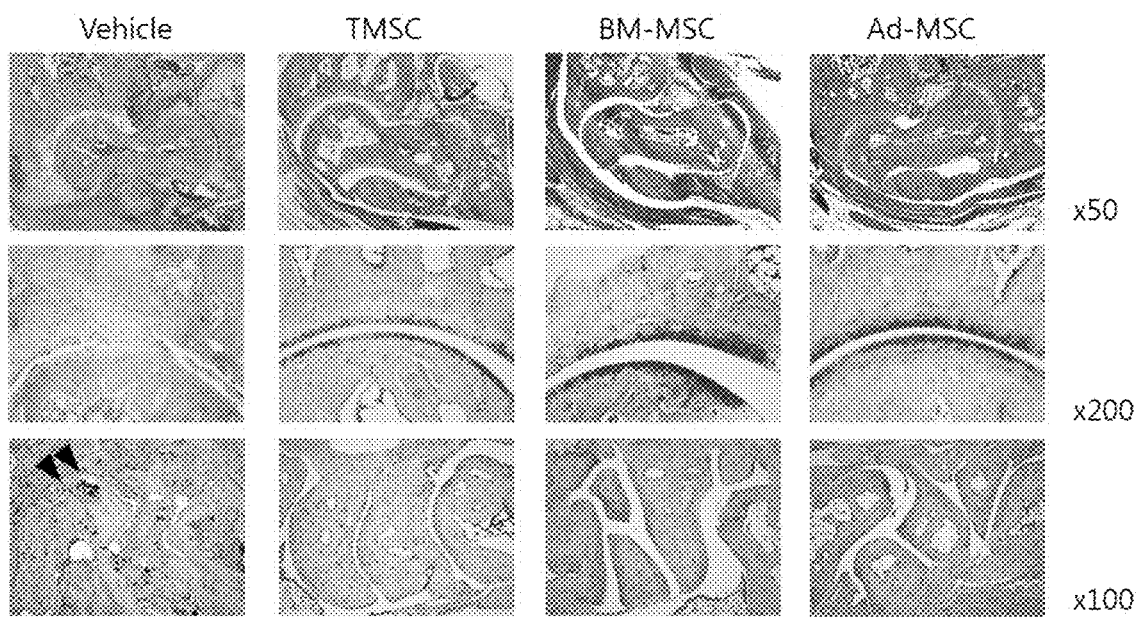
FIG. 12 illustrates the results of staining joint sections with hematoxylin and eosin (H&E), safranin O, or tartrate alkaline phosphatase in a collagen-induced arthritis animal model after administration of nasal inferior turbinate-derived mesenchymal stem cells (TMSC), bone marrow-derived mesenchymal stem cells (BM-MSC), and adipose-derived mesenchymal stem cells (Ad-MSC).

Comparison of Joint Destruction-Inhibitory Effects Upon Administration of Mesenchymal Stem Cells Derived from Different Tissue Source in Collagen-Induced Arthritis Animal Model To compare joint destruction-inhibitory effects when nasal inferior turbinate-derived mesenchymal stem cells and mesenchymal stem cells derived from other tissue source were administered to a collagen-induced arthritis animal model, injection for primary immunization was performed, and then joints were collected 9 weeks later. 5 μm joint sections were observed by staining with hematoxylin and eosin (H&E) (upper row of FIG. 12), articular chondrocytes were observed by staining with safranin O (middle row of FIG. 12), and bone tissue from which calcium was removed to identify osteoclasts was observed by staining with tartrate alkaline phosphatase (lower row of FIG. 12).

As a result, it was confirmed that the nasal inferior turbinate-derived mesenchymal stem cells exhibited the effects of suppressing pannus inflammation infiltration in joints, the loss of cartilage, and an increase in osteoclasts, which were the same levels as those of bone marrow-derived mesenchymal stem cells and adipose-derived mesenchymal stem cells (see FIG. 12).

Example 13

Comparison of Effects of Inhibiting Pathologic T Cells and Enhancing Regulatory T Cells Upon Administration of Mesenchymal Stem Cells Derived from Different Tissue Source in Collagen-Induced Arthritis Animal Model To compare the effects of inhibiting pathologic T cells (Th1 and Th17 cells) and enhancing regulatory T cells when nasal inferior turbinate-derived mesenchymal stem cells and mesenchymal stem cells derived from different sites were administered to a collagen-induced arthritis animal model, injection for primary immunization was performed, and after 9 weeks, single cells were isolated from the spleen and lymph nodes. The pathologic T cells were isolated from the spleen and the regulatory T cells were isolated from lymph nodes, and analysis was performed thereon using the method of Example 1-7.

Figure 13A:
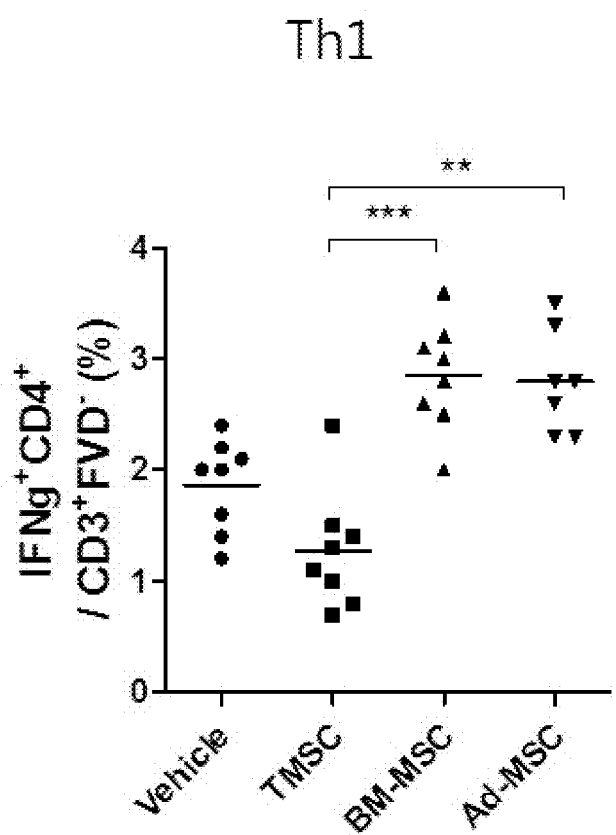
FIG. 13A illustrates Th1, $IFN\gamma^+CD4^+/CD3^+FVD^-$ cell fraction results obtained through flow cytometry in a collagen-induced arthritis animal model after administration of nasal inferior turbinate-derived mesenchymal stem cells (TMSC), bone marrow-derived mesenchymal stem cells (BM-MSC), and adipose-derived mesenchymal stem cells (Ad-MSC).
Figure 13B:
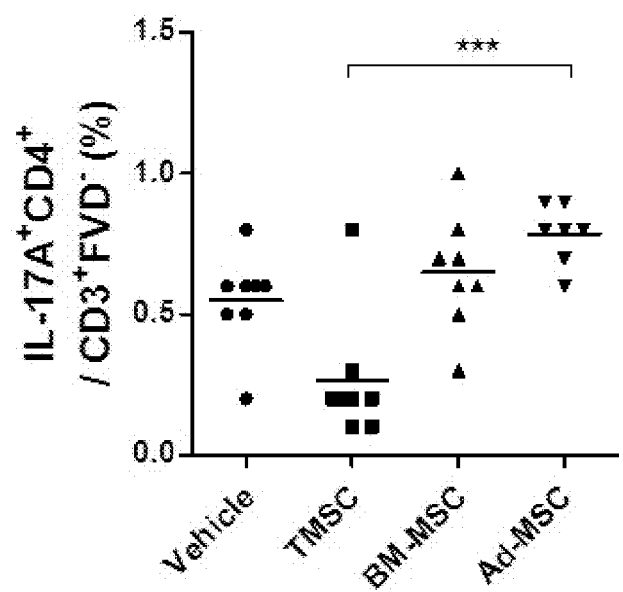
FIG. 13B illustrates Th17, $IL-17A^+CD4^+/CD3^+FVD^-$ cell fraction results obtained through flow cytometry in a collagen-induced arthritis animal model after administration of nasal inferior turbinate-derived mesenchymal stem cells (TMSC), bone marrow-derived mesenchymal stem cells (BM-MSC), and adipose-derived mesenchymal stem cells (Ad-MSC).
Figure 13C:
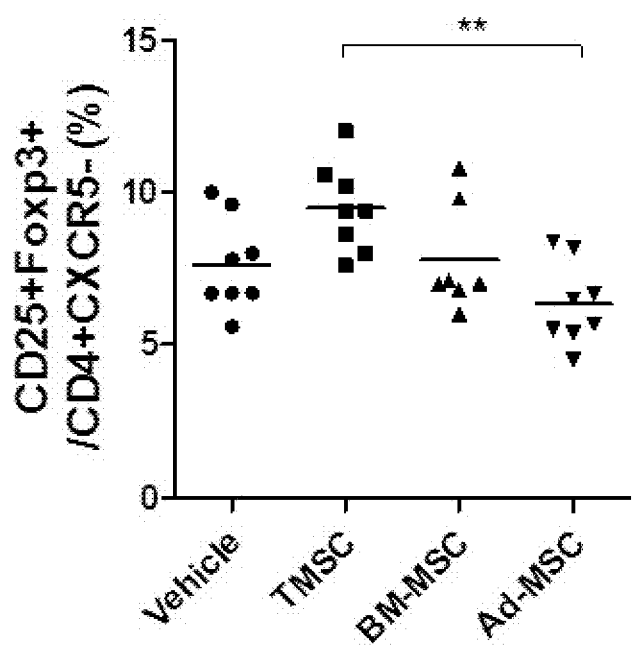
FIG. 13C illustrates Treg, $CD25^+Foxp3^+/CD4^+CXCR5^-$ cell fraction results obtained through flow cytometry in a collagen-induced arthritis animal model after administration of nasal inferior turbinate-derived mesenchymal stem cells (TMSC), bone marrow-derived mesenchymal stem cells (BM-MSC), and adipose-derived mesenchymal stem cells (Ad-MSC).

As a result, as shown in FIG. 13, it was confirmed that, in the case of the spleen cell population, inflammatory cells (Th1, IFNγ$^+$CD4$^+$/CD3$^+$FVD$^-$ cells, Th17, IL-17A$^+$CD4$^+$/CD3$^+$FVD$^-$ cells) were reduced more in the case of administration of nasal inferior turbinate-derived mesenchymal stem cells than in the case of administration of bone marrow-derived mesenchymal stem cells or adipose-derived mesenchymal stem cells (see FIGS. 13A and 13B), and it was confirmed that regulatory T cells (Treg, CD25$^+$Foxp3$^+$/CD4$^+$CXCR5$^-$ cells) contributing to immune tolerance among lymph node cells were increased more in the case of administration of nasal inferior turbinate-derived mesenchymal stem cells than in the case of administration of mesenchymal stem cells derived from other tissue source ( $P<0.01$, * $P<0.001$) (see FIG. 13C).

Example 14

Comparison of Interleukin-10-Producing T Cells in Lymph Nodes of Animal Models Administered Mesenchymal Stem Cells Derived from Different Tissue Source To compare in increase of interleukin-10-producing T cells when nasal inferior turbinate-derived mesenchymal stem cells and mesenchymal stem cells derived from other tissue source were administered to collagen-induced arthritis animal models, the inguinal/armpit lymph nodes were isolated and dispensed into a 24-well plate coated with 0.5 μg/ml of an anti-CD3 cross-linking antibody at a density of 1×10⁶ cells/well. In addition, 1 μg/mL of an anti-CD28 crosslinking antibody was added thereto and cultured for 3 days, and the production of interleukin-10 was confirmed by ELISA.

Figure 14:
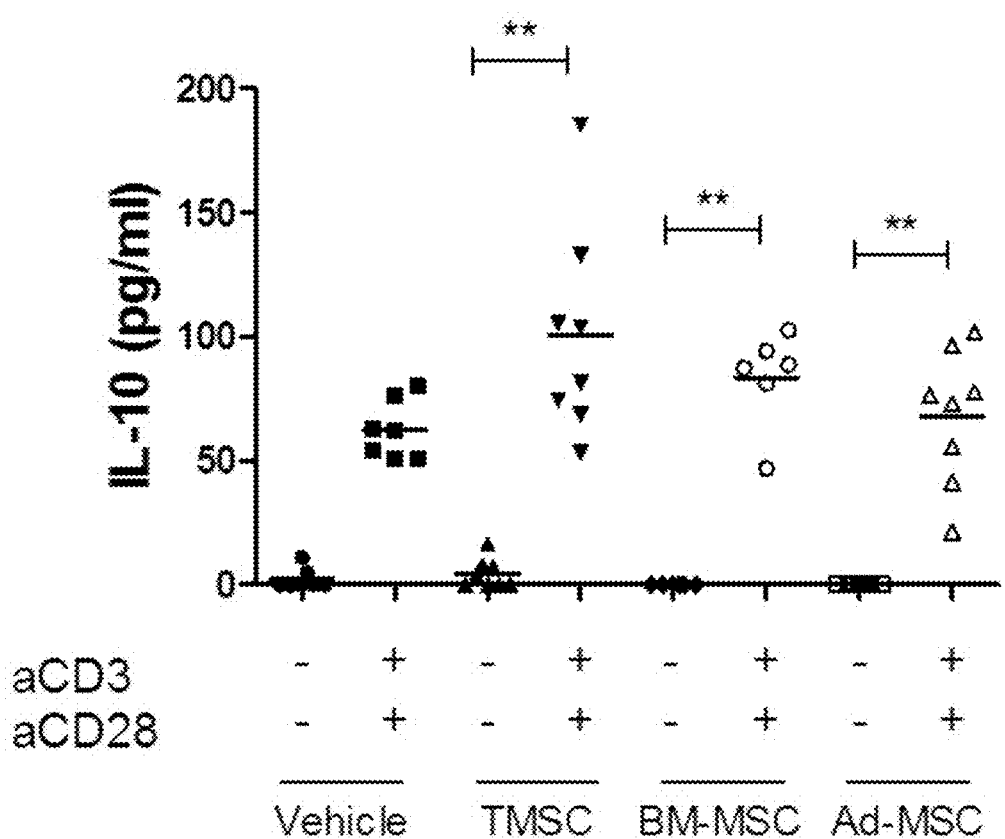
FIG. 14 illustrates the distribution of interleukin-10-producing T cells in lymph nodes of animal models administered nasal inferior turbinate-derived mesenchymal stem cells (TMSC), bone marrow-derived mesenchymal stem cells (BM-MSC), and adipose mesenchymal stem cells (Ad-MSC).

As a result, as shown in FIG. 14, it was confirmed that, when the lymph node T cells were stimulated with aCD3 and aCD28 antibodies, the frequency of inflammation-inhibitory interleukin-10-producing T cells was highest in the case of administration of the nasal inferior turbinate-derived mesenchymal stem cells.

Example 15

Comparison of Human Peripheral Blood $CD4^+$ T Cell Proliferation Inhibitory Activity Using Mesenchymal Stem Cells from Different Origins The degrees of inhibition of proliferation of $CD4^+CD25^-$ T cells isolated from human peripheral blood of nasal inferior turbinate-derived mesenchymal stem cells and mesenchymal stem cells derived from other origin were compared using the method of Example 1-10.

Figure 15A:
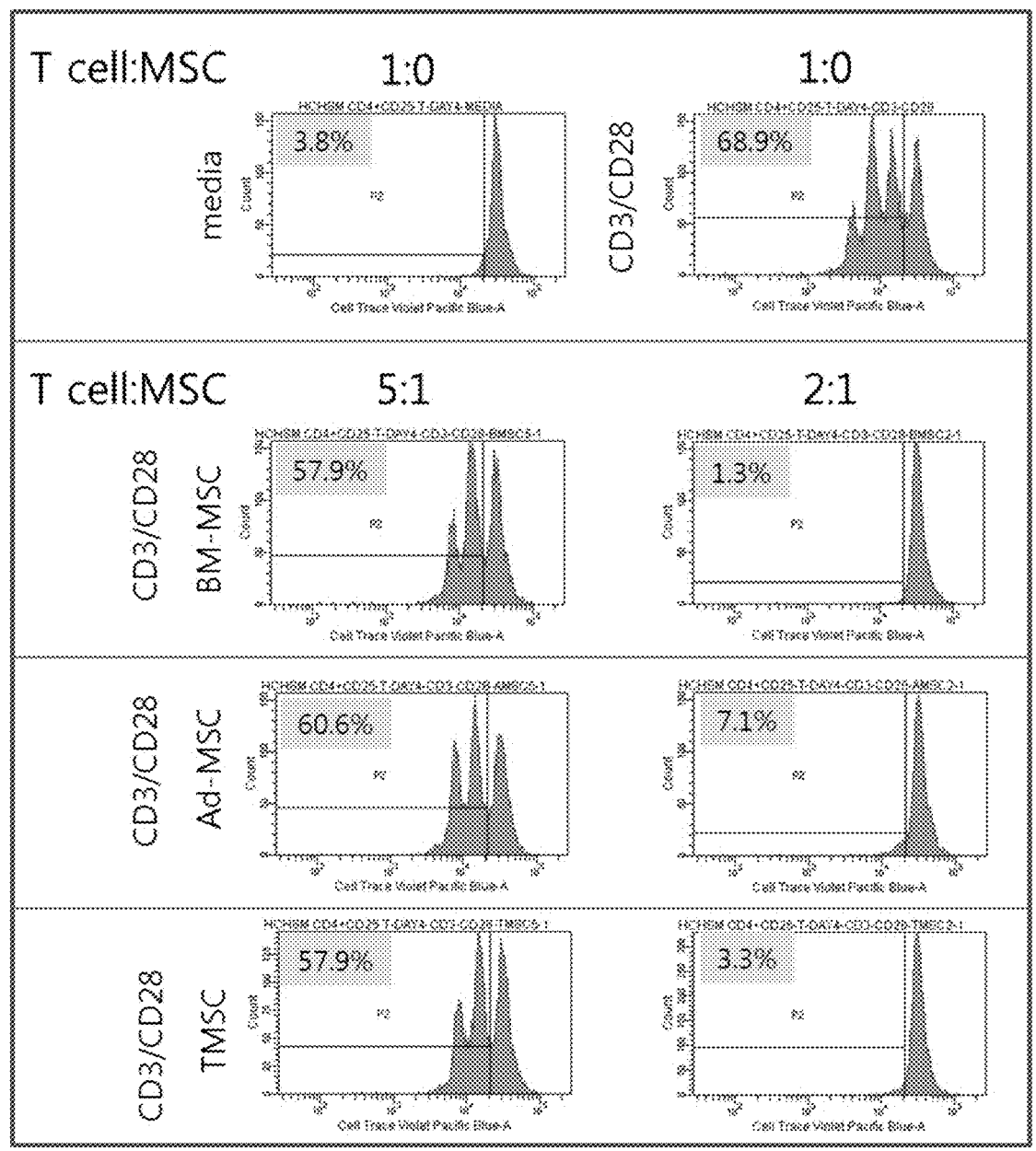
FIG. 15A is a set of histograms illustrating the results showing the abilities of nasal inferior turbinate-derived mesenchymal stem cells (TMSC), bone marrow-derived mesenchymal stem cells (BM-MSC), and adipose-derived mesenchymal stem cells (Ad-MSC) to inhibit the proliferation of human peripheral blood CD4+ T cells.
Figure 15B:
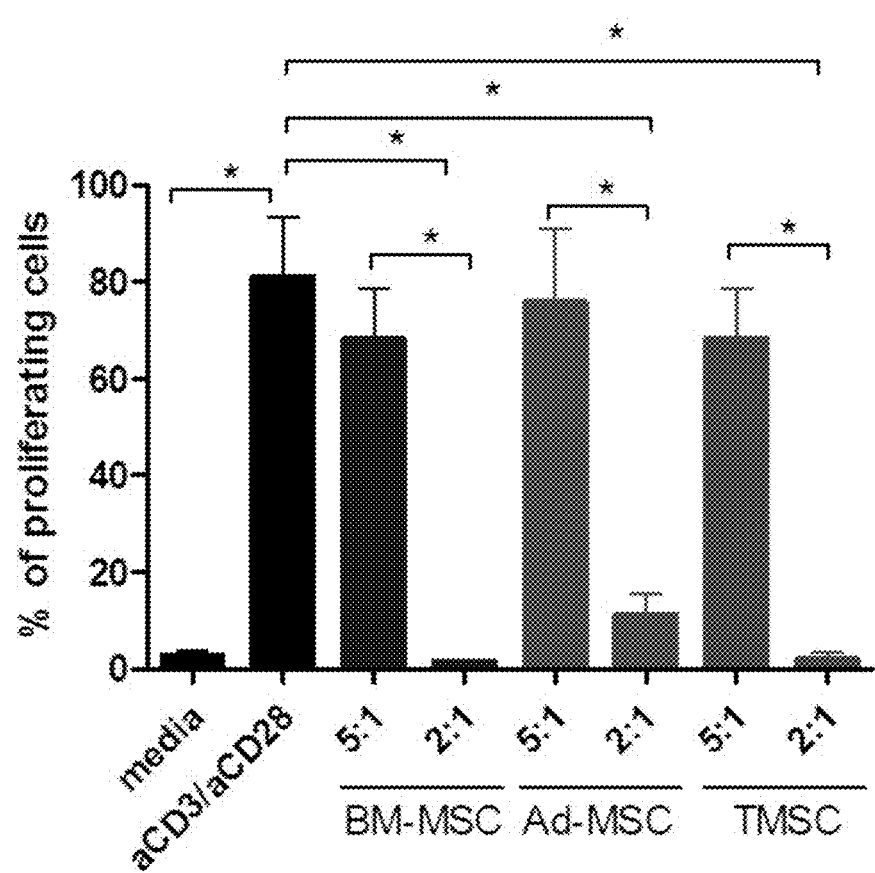
FIG. 15B is a graph summarizing the results of FIG. 15A.

As a result, as shown in FIGS. 15A and 15B, it was confirmed that the nasal inferior turbinate-derived mesenchymal stem cells exhibited the same T cell proliferation inhibitory ability as that of bone marrow-derived mesenchymal stem cells or adipose-derived mesenchymal stem cells (see FIGS. 15A and 15B).

Example 16

Confirmation of Increase in Indoleamine-2,3-dioxygenase (IDO) Expression Upon Treatment of Nasal Inferior Turbinate-Derived Mesenchymal Stem Cells (TMSC) with Interferon-Gamma (IFNg)

IDO is involved in the inhibition of T cell proliferation of existing stem cells, which is induced by interferon-gamma. Thus, to confirm the same effect also in nasal inferior turbinate-derived mesenchymal stem cells, the nasal inferior turbinate-derived mesenchymal stem cells were stimulated for 24 hours by treatment with 10 ng/ml of interferon-gamma and IDO expression was analyzed by real-time RT-PCR according to the method of Example 1-11.

Figure 16:
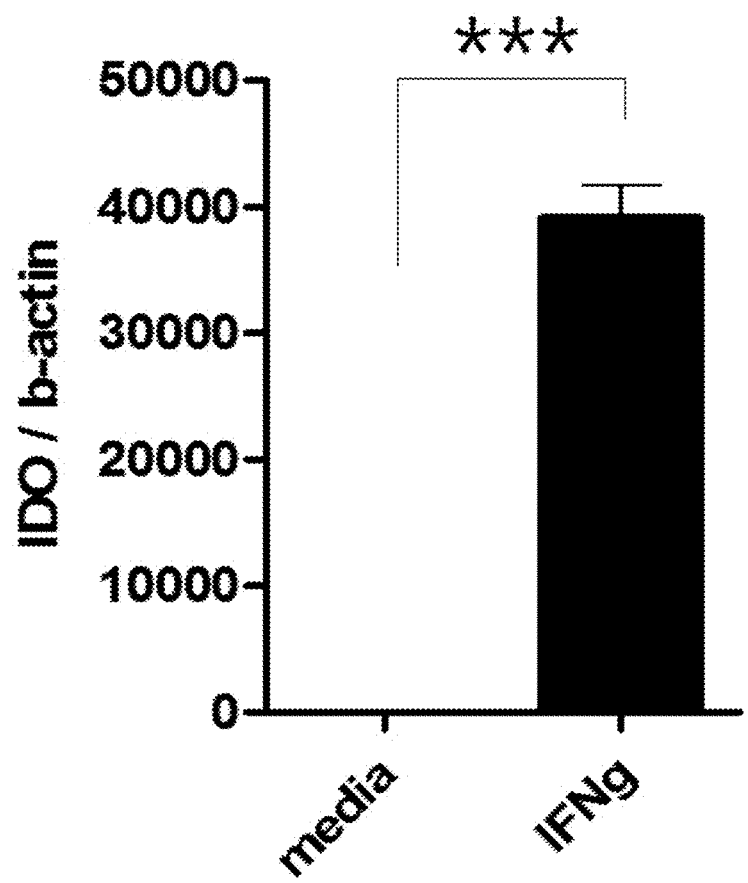
FIG. 16 illustrates a relative expression level of indoleamine-2,3-dioxygenase (IDO) mRNA when nasal inferior turbinate-derived mesenchymal stem cells (TMSC) were stimulated with interferon-gamma.

As a result, as shown in FIG. 16, it was confirmed that IDO mRNA expression was significantly increased by interferon-gamma treatment even in the nasal inferior turbinate-derived mesenchymal stem cells.

Example 17

Confirmation of Decrease in T Cell Proliferation Inhibitory Activity According to Treatment with 1-Methyl-L-Tryptophan (1MT) Upon Co-Culture of Nasal Inferior Turbinate-Derived Mesenchymal Stem Cells (TMSC) and T Cells To determine whether IDO is involved in the mechanism of suppressing T cell proliferation of nasal inferior turbinate-derived mesenchymal stem cells, the TMSCs were pre-treated with 1MT upon co-culture of healthy human T cells and TMSCs. After 6 days, the T cells were subjected to flow cytometry as in Example 1-10, and the bars of bar graphs of FIG. 17 represents the mean±standard deviation (SD) of three experiments.

Figure 17A:
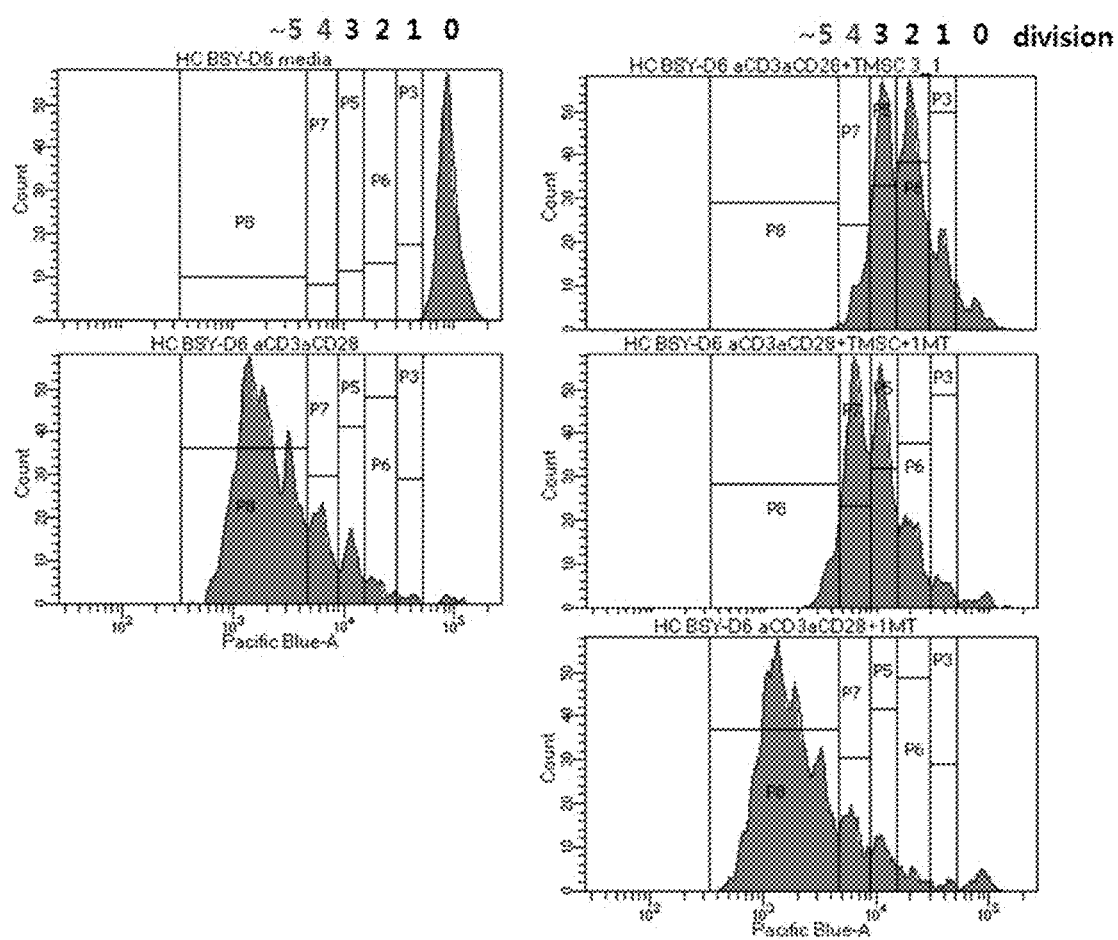
FIG. 17A illustrates T cell proliferation inhibitory capacity through flow cytometry when T cells and 1-methyl-L-tryptophan (1MT) were co-cultured with nasal inferior turbinate-derived mesenchymal stem cells (TMSC).
Figure 17B:
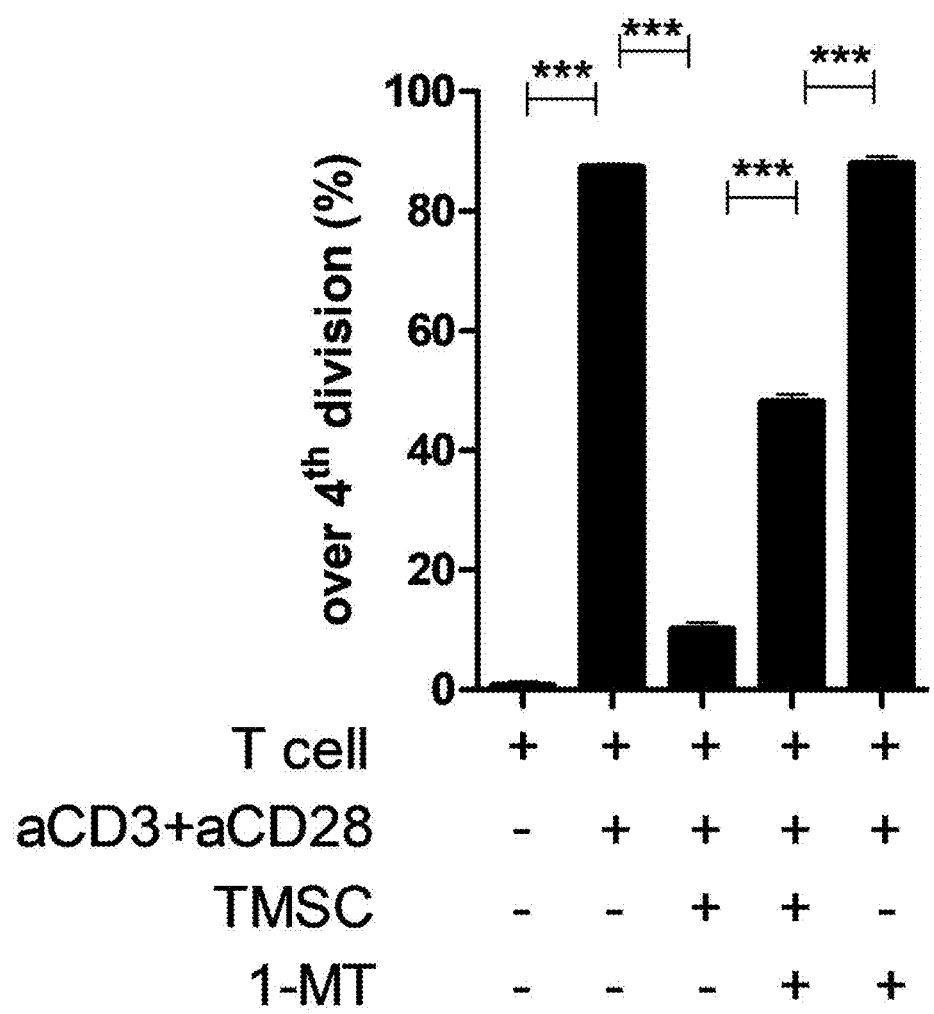
FIG. 17B is a graph summarizing the results of FIG. 17A.

As a result, as shown in FIGS. 17A and 17B, when 1MT, which inhibits the function of IDO, was not used for treatment, the nasal inferior turbinate-derived mesenchymal stem cells exhibited excellent T cell proliferation inhibitory activity, but the T cell proliferation inhibitory activity was partially lost upon treatment with 1MT. The above results mean that IDO is involved in the T cell proliferation inhibition mechanism of the nasal inferior turbinate-derived mesenchymal stem cell.

The foregoing description of the present invention is provided for illustrative purposes only, and it will be understood by those of ordinary skill in the art to which the present invention pertains that the present invention may be easily modified into other particular forms without changing the technical spirit or essential characteristics of the present invention. Thus, the above-described embodiments should be construed as being provided for illustrative purposes only and not for purposes of limitation.

INDUSTRIAL APPLICABILITY

While existing mesenchymal stem cells are accompanied by severe pain in an acquisition process and are time-consuming and cost-consuming in a process of culturing a sufficient amount thereof, nasal inferior turbinate-derived mesenchymal stem cells according to the present invention can be safely acquired and obtained in a sufficient amount at a desired time, and thus mesenchymal stem cells can be obtained at low cost with high efficiency, and has the same genetic origin as that of a subject to which the cell is administered, thus causing reduced occurrence of side effects and exhibiting the same effects as or superior effects to those of bone marrow-derived mesenchymal stem cells or adipose-derived mesenchymal stem cells, and accordingly, the nasal inferior turbinate-derived mesenchymal stem cells are effective in individually customized immunocompatible rheumatoid arthritis prevention or treatment and can be usefully used in the medical industry field for the development of a rheumatoid arthritis therapeutic agent.

What is claimed is:

1. A method of treating rheumatoid arthritis, the method comprising administering, to a subject in need thereof, a pharmaceutical composition comprising nasal inferior turbinate-derived mesenchymal stem cells as an active ingredient,
   wherein the nasal inferior turbinate-derived mesenchymal stem cells reduce interleukin-17A; and
   wherein the nasal inferior turbinate-derived mesenchymal stem cells are in the form of fusiform.

2. The method of claim 1, wherein the rheumatoid arthritis is collagen-induced arthritis.

3. The method of claim 1, wherein the administration of the nasal inferior turbinate-derived mesenchymal stem cells reduces immunoglobulin G2a (IgG2a) in the subject, wherein the IgG2a is an inflammation-inducing factor.

4. The method of claim 1, wherein the administration of the nasal inferior turbinate-derived mesenchymal stem cells increases regulatory T cells contributing to immune tolerance among spleen cells in the subject.

5. The method of claim 1, wherein the administration of the nasal inferior turbinate-derived mesenchymal stem cells reduces the proliferative ability of lymph node T cells in the subject.

6. The method of claim 1, wherein the administration of the nasal inferior turbinate-derived mesenchymal stem cells reduces tumor necrosis factor-$\alpha$ in the subject.

7. The method of claim 1, wherein the administration of the nasal inferior turbinate-derived mesenchymal stem cells increases interleukin-10 in the subject.

8. The method of claim 1, wherein the administration of the nasal inferior turbinate-derived mesenchymal stem cells inhibits the proliferation of $CD4^+$ T cells in the subject.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: IDO(indoleamine-2,3-dioxygenase) forward primer

<400> SEQUENCE: 1
gccaactctc caagaaactg                                                 20
```

```
<210> SEQ ID NO 2
<211> LENGTH: 20
<212> TYPE: DNA
<213> ORGANISM: Artificial Sequence
<220> FEATURE:
<223> OTHER INFORMATION: IDO(indoleamine-2,3-dioxygenase) reverse primer

<400> SEQUENCE: 2
gcagtctcca tcacgaaatg                                              20

<210> SEQ ID NO 3
<211> LENGTH: 20
<212> TYPE: DNA
<213> ORGANISM: Artificial Sequence
<220> FEATURE:
<223> OTHER INFORMATION: beta actin forward primer

<400> SEQUENCE: 3
ggacttcgag caagagatgg                                              20

<210> SEQ ID NO 4
<211> LENGTH: 22
<212> TYPE: DNA
<213> ORGANISM: Artificial Sequence
<220> FEATURE:
<223> OTHER INFORMATION: beta actin reverse primer

<400> SEQUENCE: 4
tgtgttgggg tacaggtctt tg                                           22
```